United States Patent [19]
Dubrow et al.

[11] Patent Number: 5,932,428
[45] Date of Patent: *Aug. 3, 1999

[54] METHOD FOR PREPARING A SAMPLE IN A SCAN CAPILLARY FOR IMMUNOFLUORESCENT INTERROGATION

[75] Inventors: Robert S. Dubrow, San Carlos; Bala S. Manian, Los Altos Hills, both of Calif.

[73] Assignee: Biometric Imaging, Inc., Mountain View, Calif.

[ * ] Notice: This patent is subject to a terminal disclaimer.

[21] Appl. No.: 08/739,131

[22] Filed: Oct. 28, 1996

Related U.S. Application Data

[63] Continuation of application No. 08/328,241, Oct. 24, 1994, Pat. No. 5,585,246, which is a continuation-in-part of application No. 08/236,342, May 2, 1994, Pat. No. 5,547,849, which is a continuation-in-part of application No. 08/018,762, Feb. 17, 1993, abandoned.

[51] Int. Cl.$^6$ .................................................. G01N 33/53
[52] U.S. Cl. .......................... 435/7.24; 435/7.32; 435/5; 435/6; 436/10; 436/17; 436/18
[58] Field of Search .................. 435/7.24, 7.32, 435/5, 6; 436/10, 17, 18

[56] References Cited

U.S. PATENT DOCUMENTS

| | | | |
|---|---|---|---|
| D. 366,938 | 2/1996 | Shartle et al. | D24/224 |
| 4,125,828 | 11/1978 | Resnick et al. | 356/39 |
| 4,521,518 | 6/1985 | Carter et al. | 436/10 |
| 4,783,401 | 11/1988 | Horan et al. | 435/34 |
| 5,009,503 | 4/1991 | Murphy, Jr. et al. | 356/339 |
| 5,039,487 | 8/1991 | Smith | 422/56 |
| 5,264,369 | 11/1993 | Sakata et al. | 436/63 |
| 5,284,771 | 2/1994 | Fan et al. | 436/10 |
| 5,316,951 | 5/1994 | Carver, Jr. et al. | 436/63 |
| 5,325,169 | 6/1994 | Nakamoto et al. | 356/73 |
| 5,360,739 | 11/1994 | Fan et al. | 436/63 |
| 5,585,246 | 12/1996 | Dubrow et al. | 435/7.24 |

OTHER PUBLICATIONS

Dzik et al., Flow–Cytometric Method for Counting Very Low Numbers of Leukocytes in Platelet Products, VOX SANG, 1990, 59:153–159.

Haugland, Handbook of Fluorescent Probes and Research Chemicals, 5th Edition, 1992–1994, pp. 221, 223.

Tucker et al., "Automated Densitometry of Cell Populations in a Continuous–Motion Imaging Cell Scanner," Applied Optics, Aug. 15, 1987, vol. 26. No. 16, pp. 3315–3324.

Mroz et al., "Fluorescence Analysis of Picoliter Samples," Analytical Biochemistry 102, 1980, pp. 90–96.

Landay et al., Application of Flow Cytometry to the Study of HIV Infection, AIDS, 1900, 4:479–497.

Burger et al., "Acousto–Optic Laser–Scanning Cytometer," Cytometry, 1988, 9:101–110.

Pietersz et al., "Comparison of Five Different Filters for the Removal of Leukocytes From Red Cell Concentrates," Vox Sang, 1992, 62: 76–81.

*Primary Examiner*—Donna Wortman

[57] ABSTRACT

An assay and sample mixture for the enumeration of fluorescently stained target components of a whole blood sample by an imaging instrument. The sample preparation method ensures that the amount of target components per unit of volume of the whole blood sample is preserved by elimination of certain non-quantitative preparation steps while producing an even hematocrit layer within a scan capillary. Typical target components include white blood cells that express certain surface antigens, such as CD-4 and CD-8 proteins. To inhibit aggregation of the red blood cells, a reagent is added to an aliquot of whole blood sample. The aliquot of whole blood is mixed and with a preselected amount of a fluorescent dye and ligand complex which tags the target components. The sample and fluorescent complex are allowed to incubate a sufficient amount of time to bind enough of the fluorescent complex to the target components to provide a fluorescent signal from the target components which will be distinguishable from the fluorescent signal from the unbound fluorescent complex in the sample. The resulting mixture allows the imaging instrument to detect peak intensities of fluorescence from the target components, thereby allowing the target components to be volumetrically enumerated with an improved level of accuracy and efficiency.

48 Claims, 11 Drawing Sheets

FIG._1
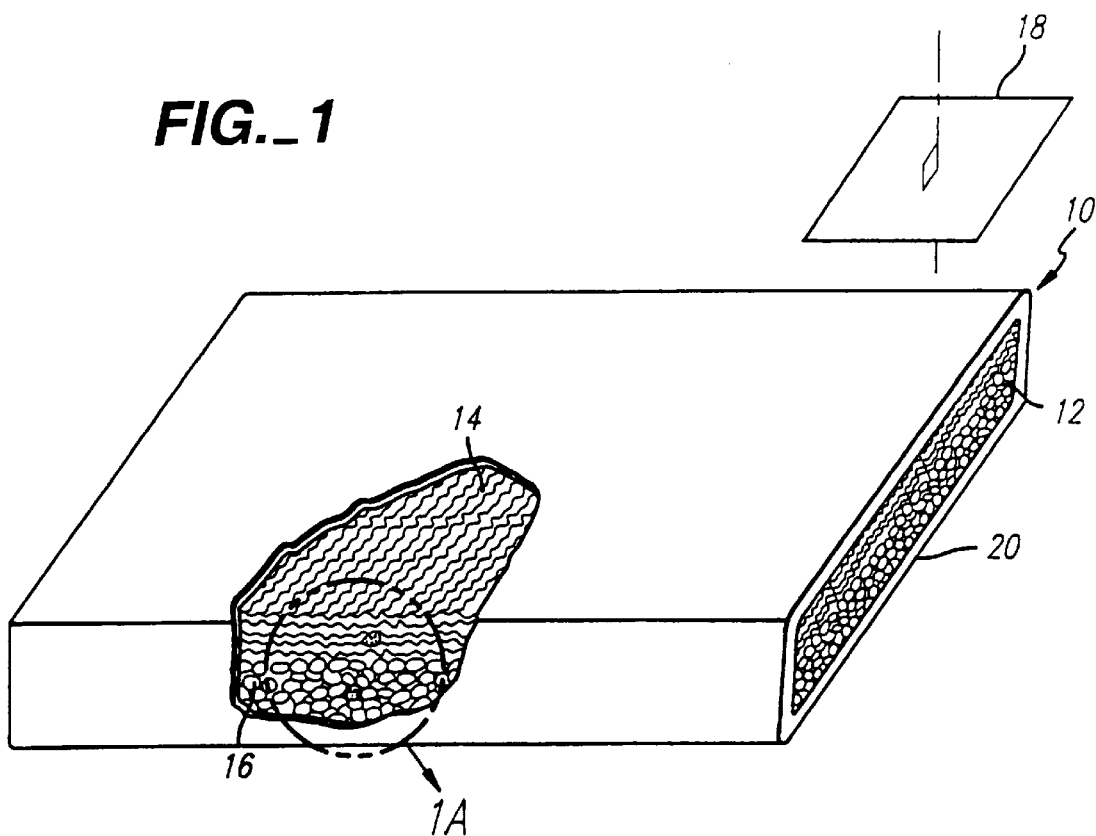
FIG._1A
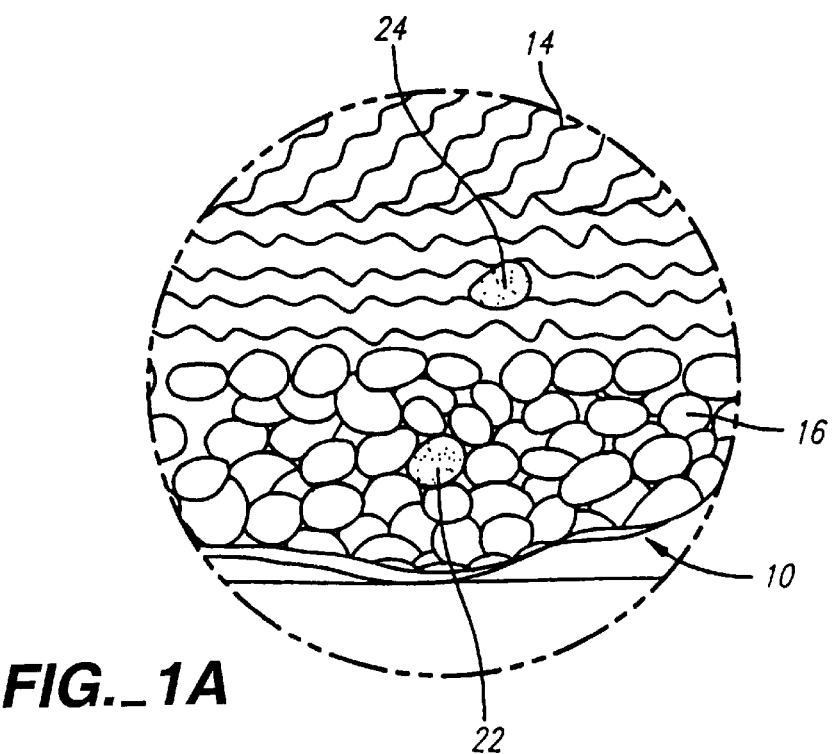

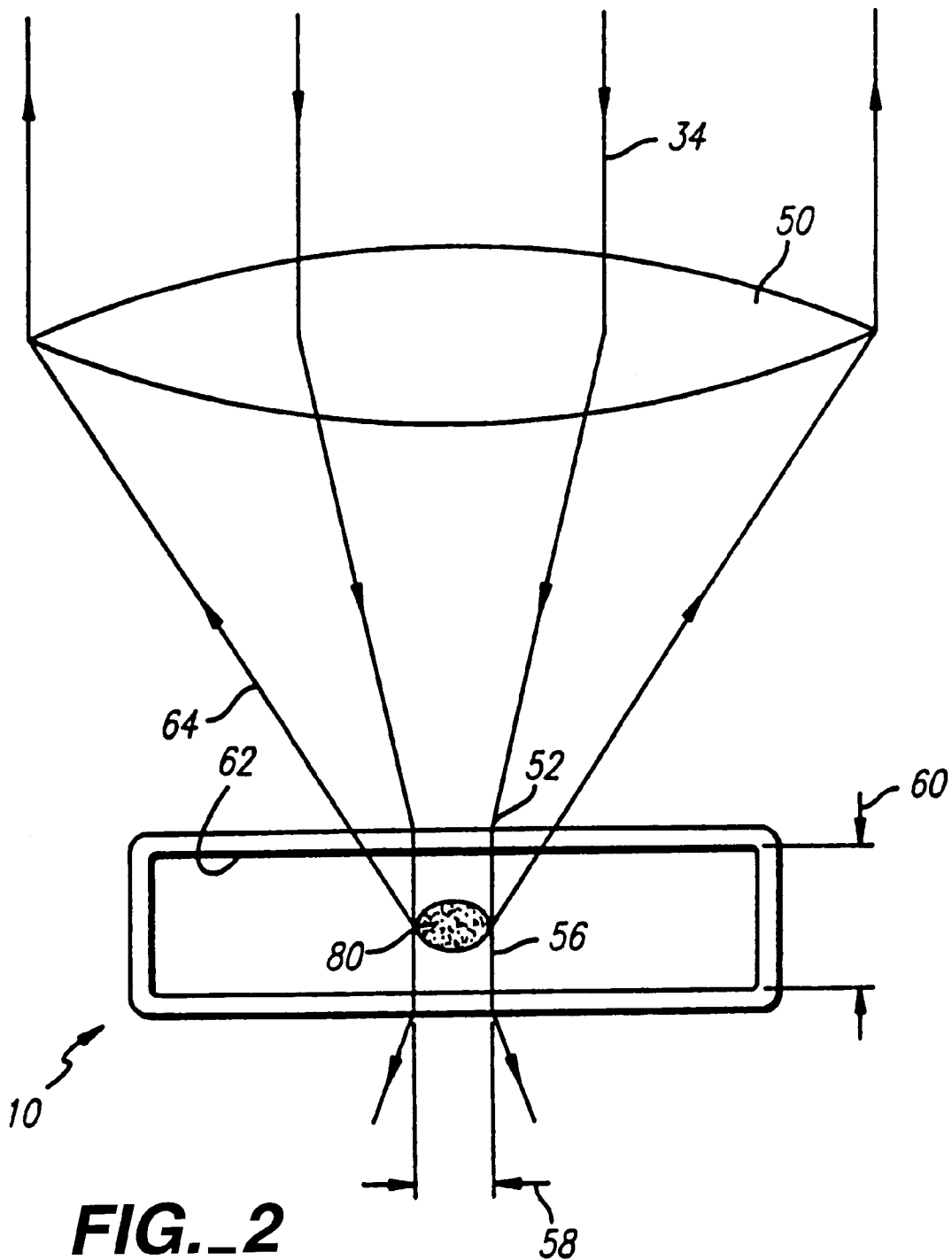
FIG._2

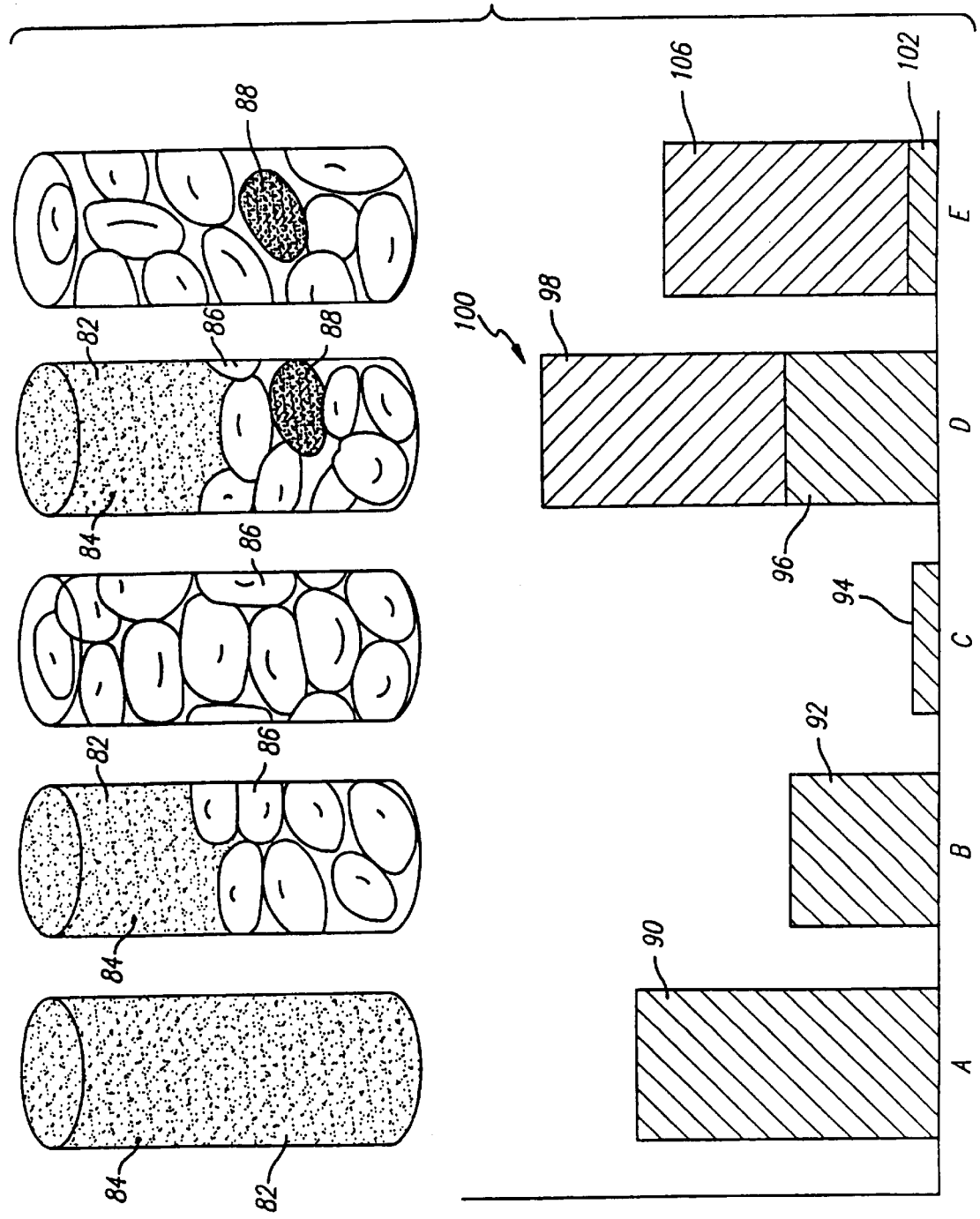
FIG._3

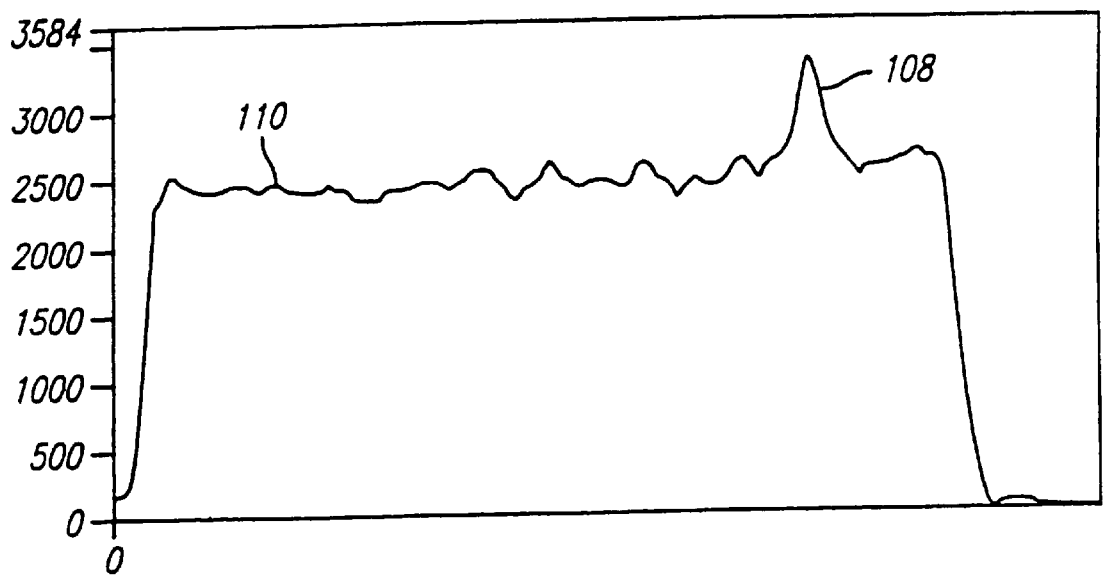
FIG._4A
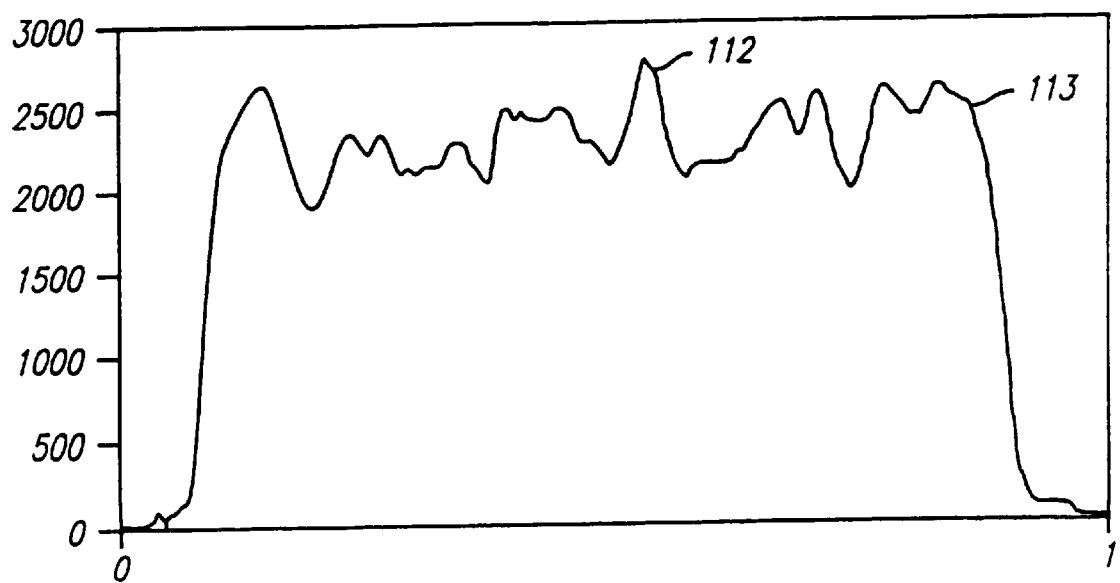
FIG._4B

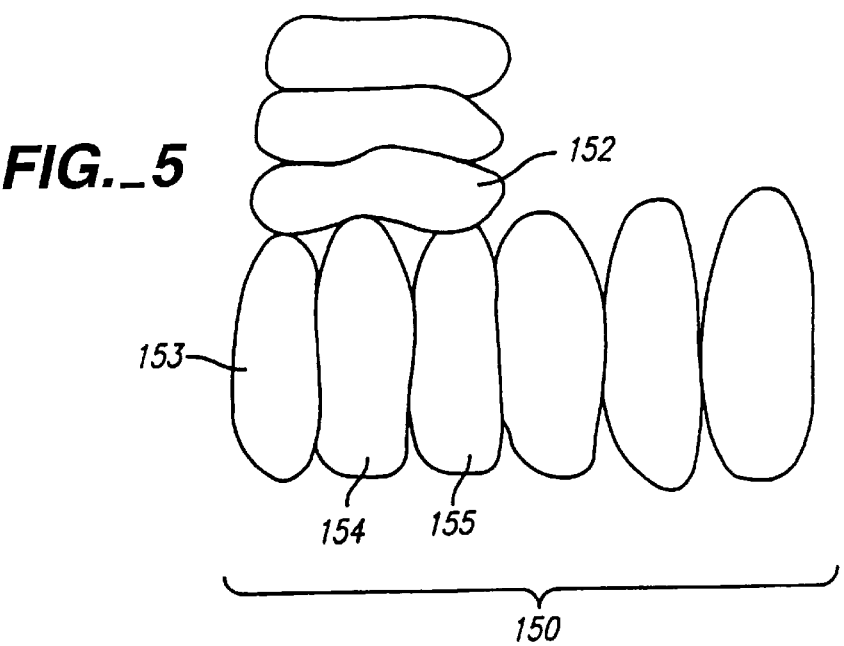
FIG._5
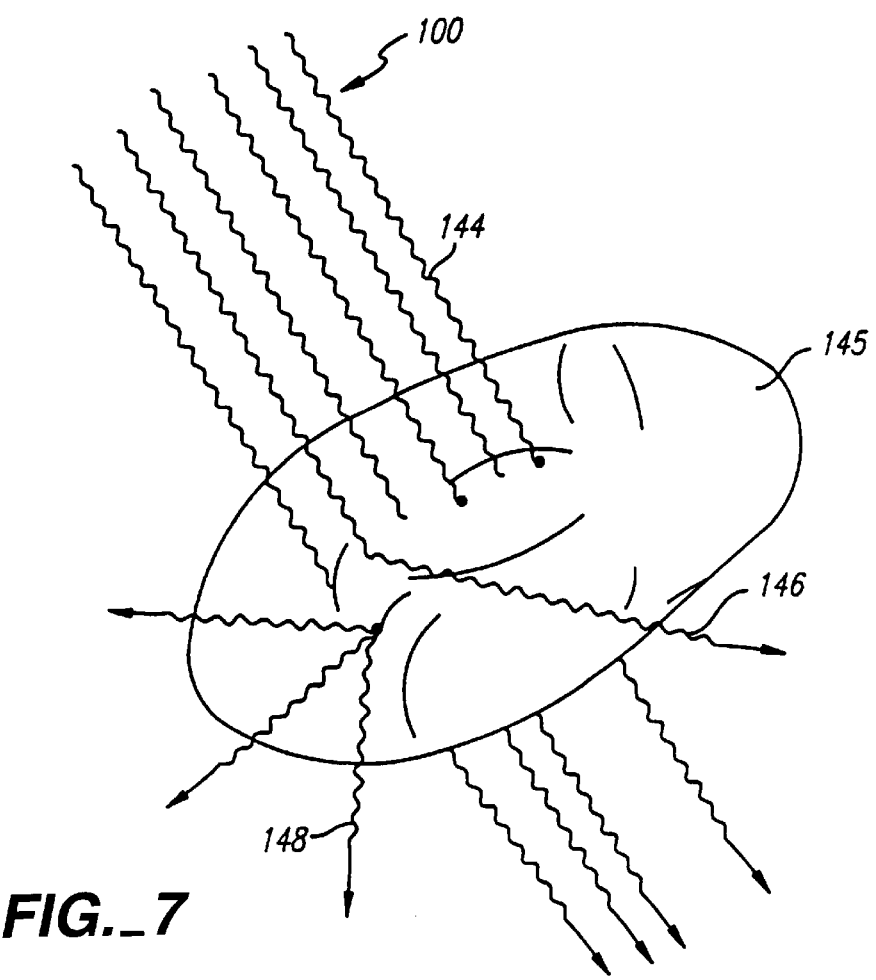
FIG._7

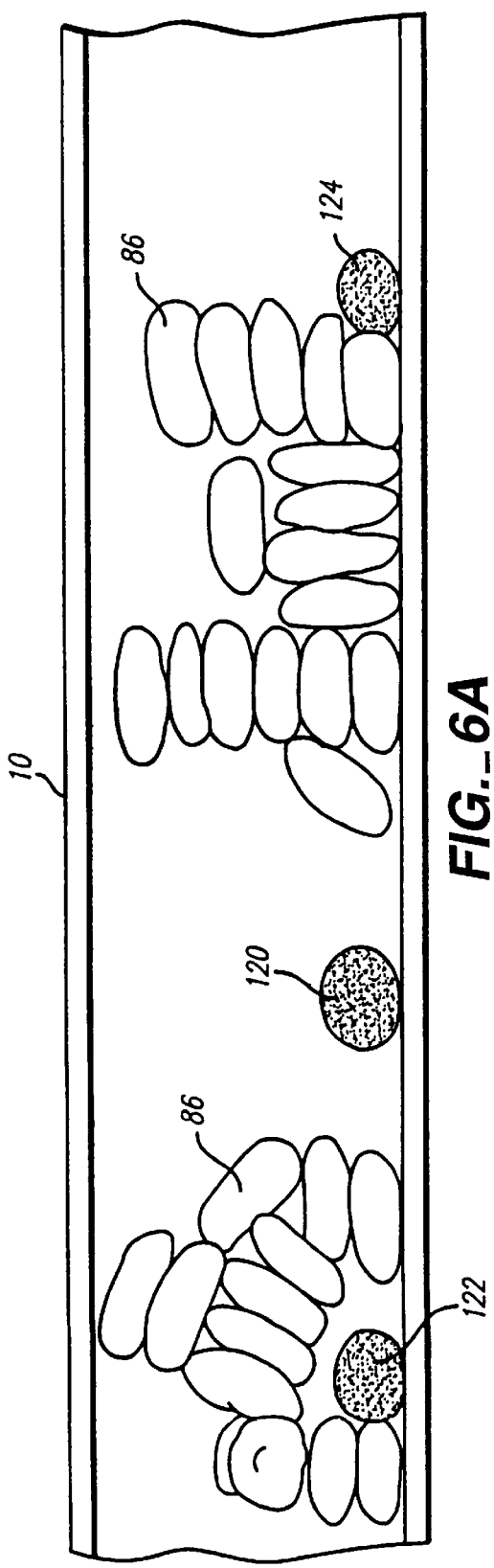
FIG._6A
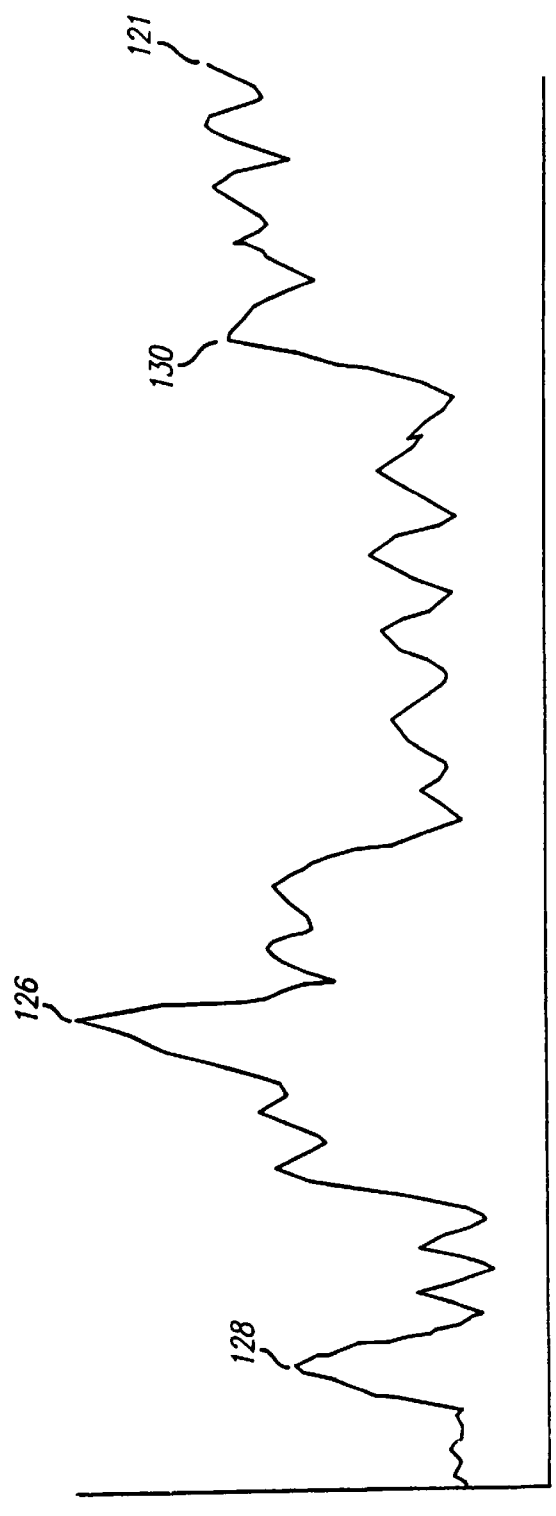
FIG._6B
RELATIVE FLUORESCENT UNITS

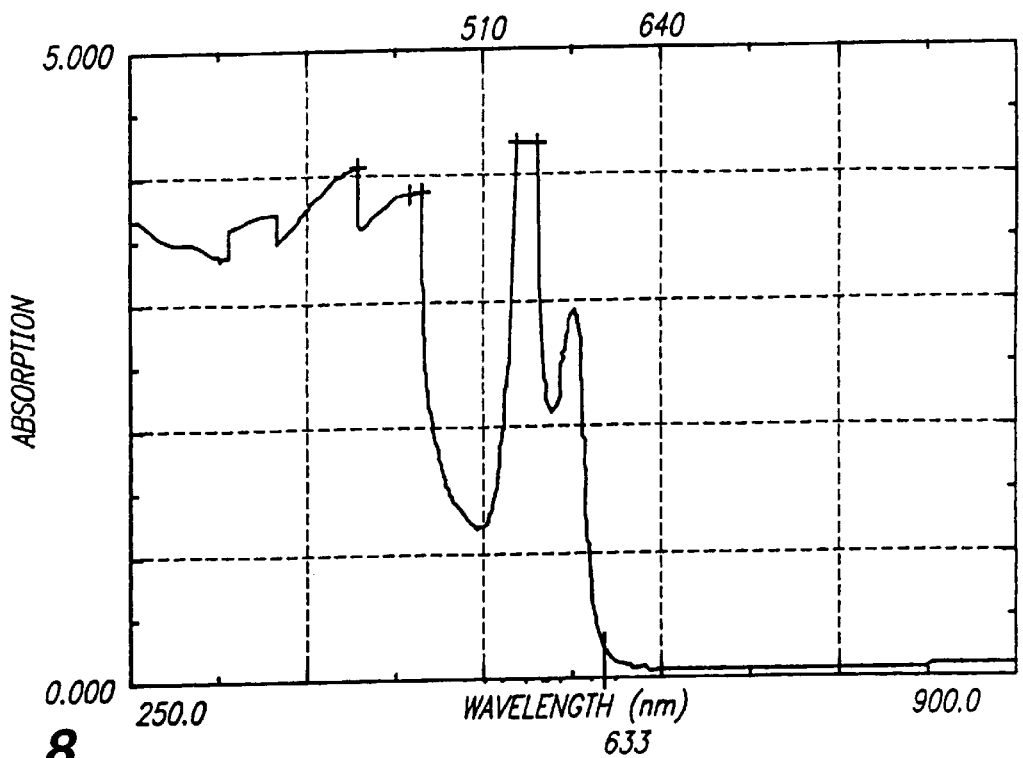
FIG._8
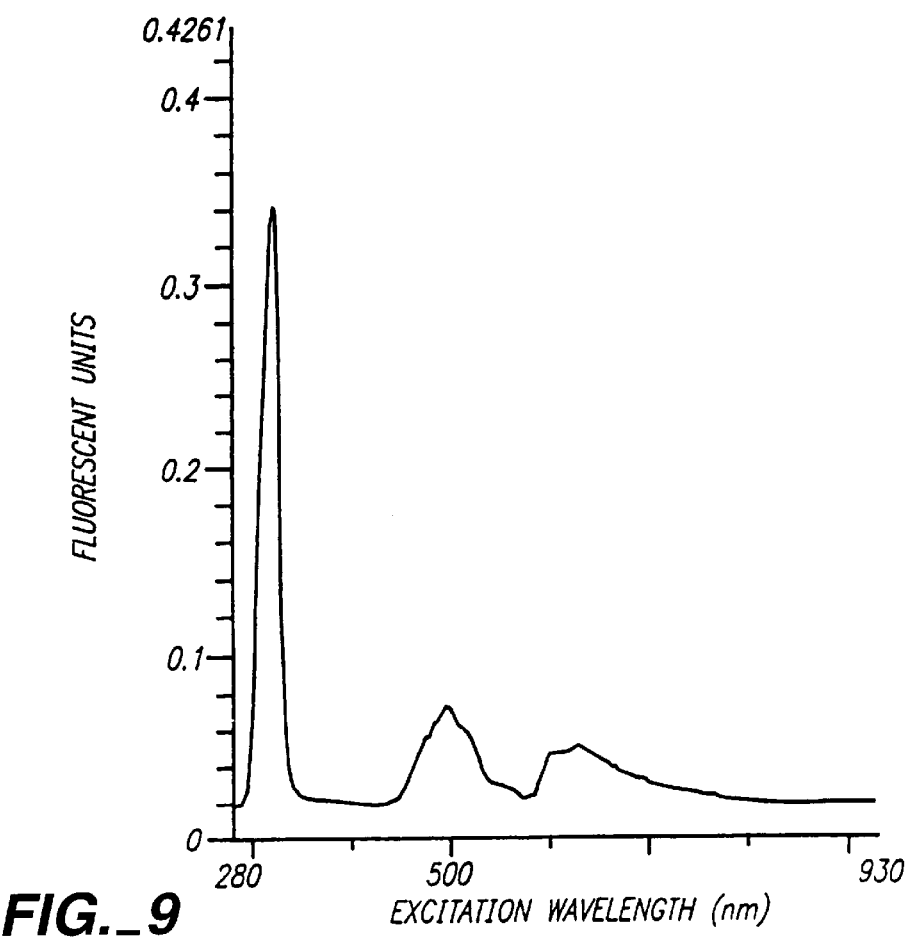
FIG._9

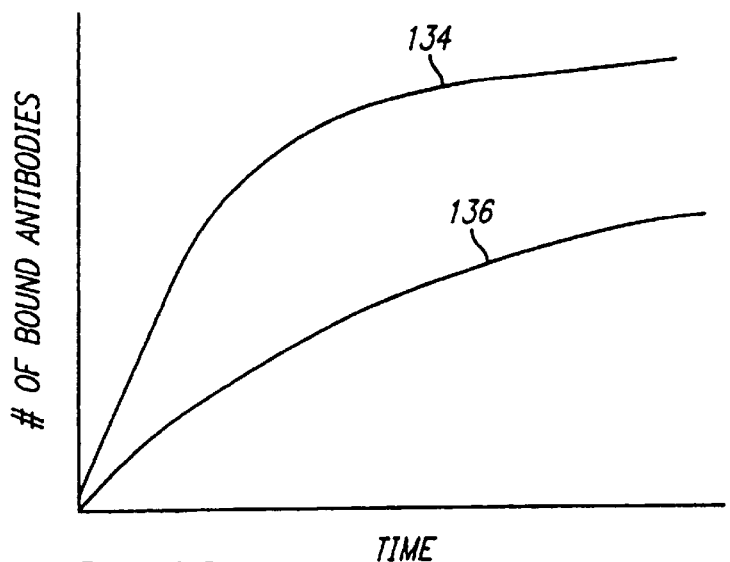
FIG._10
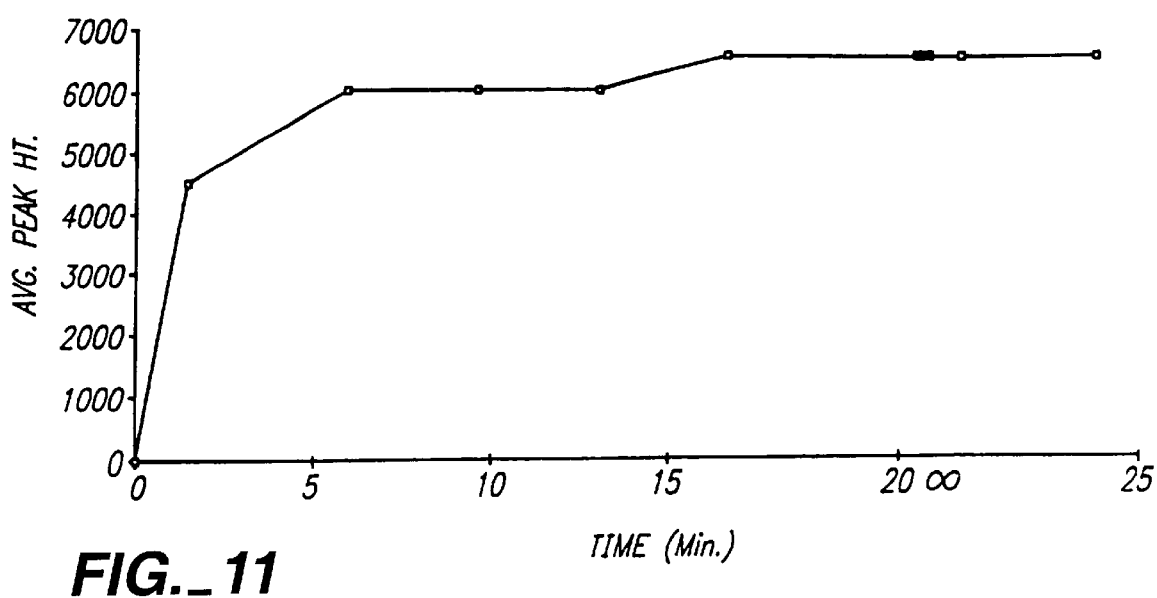
FIG._11

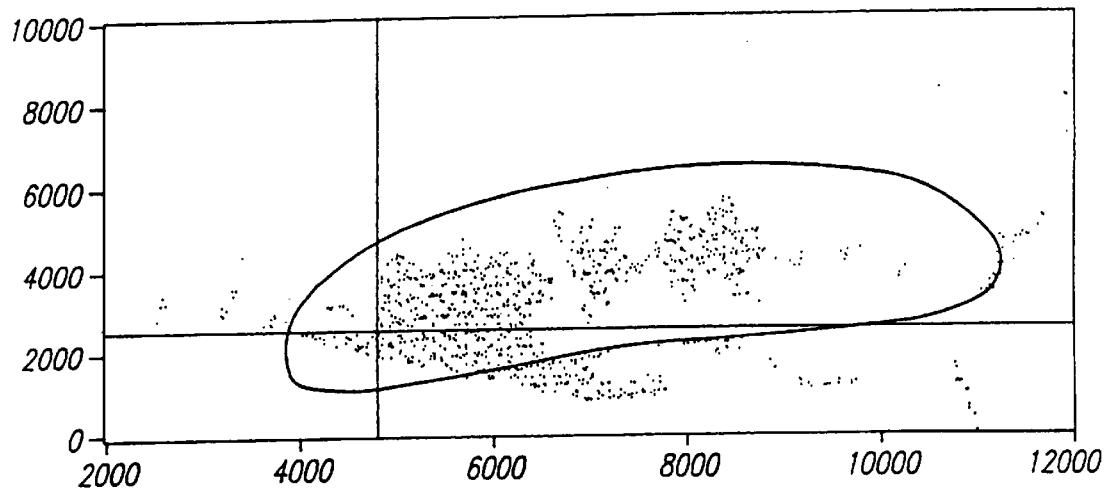
FIG._12
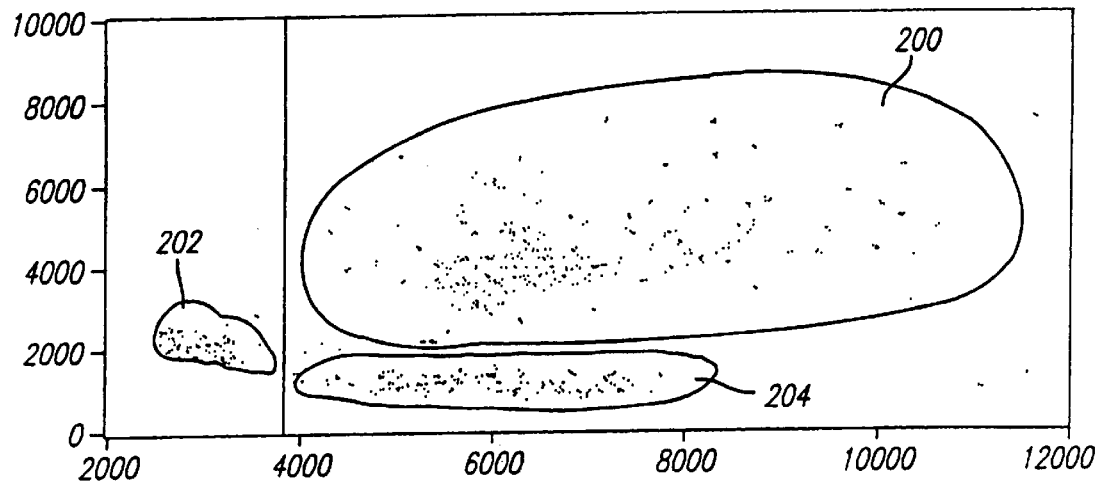
FIG._13
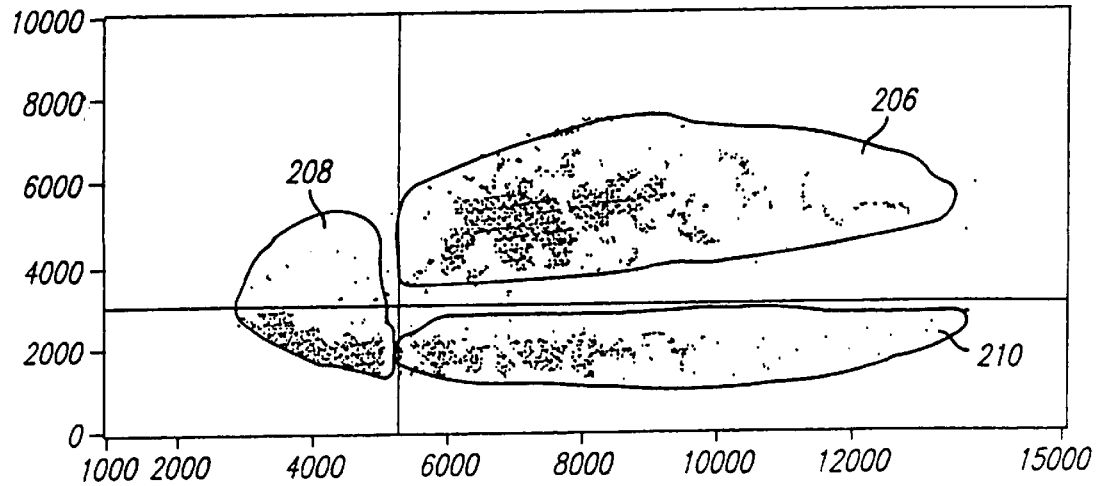
FIG._14

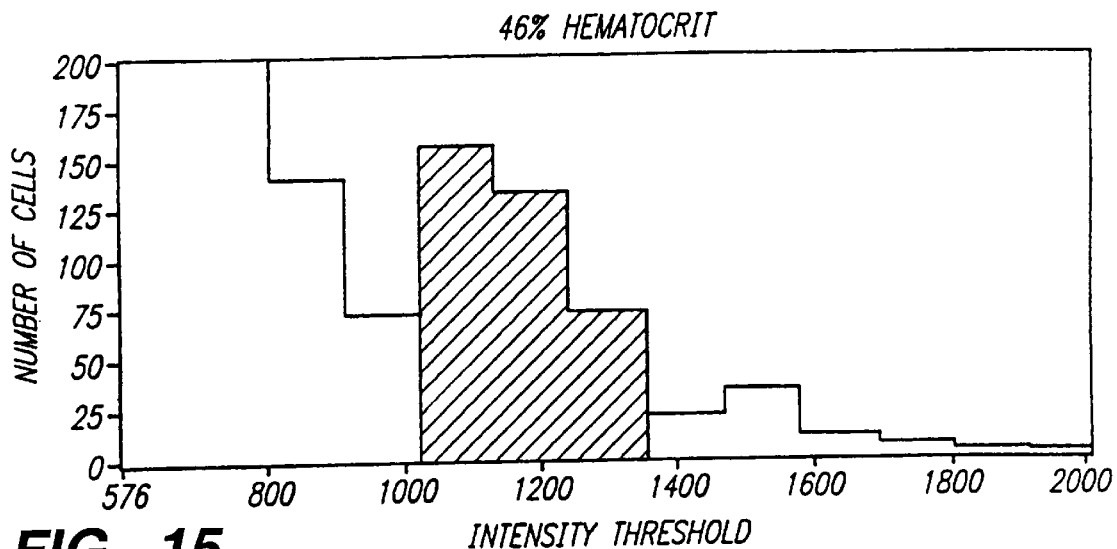
FIG._15
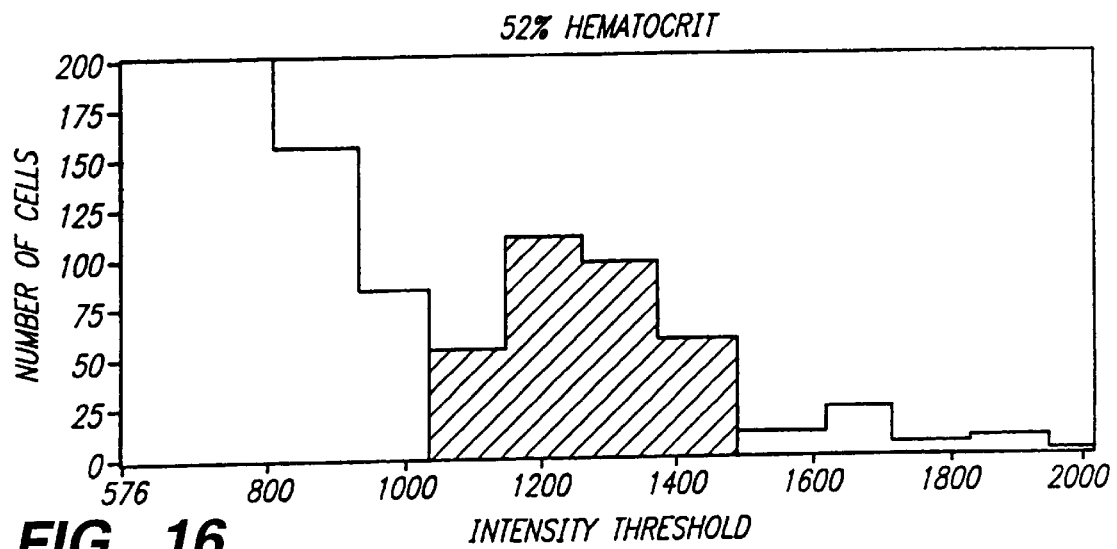
FIG._16
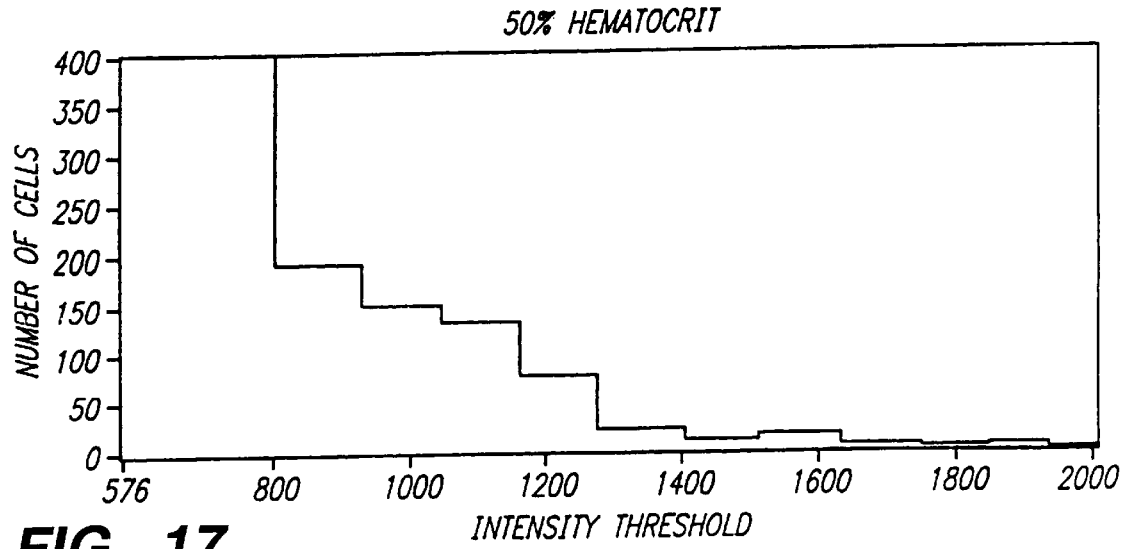
FIG._17

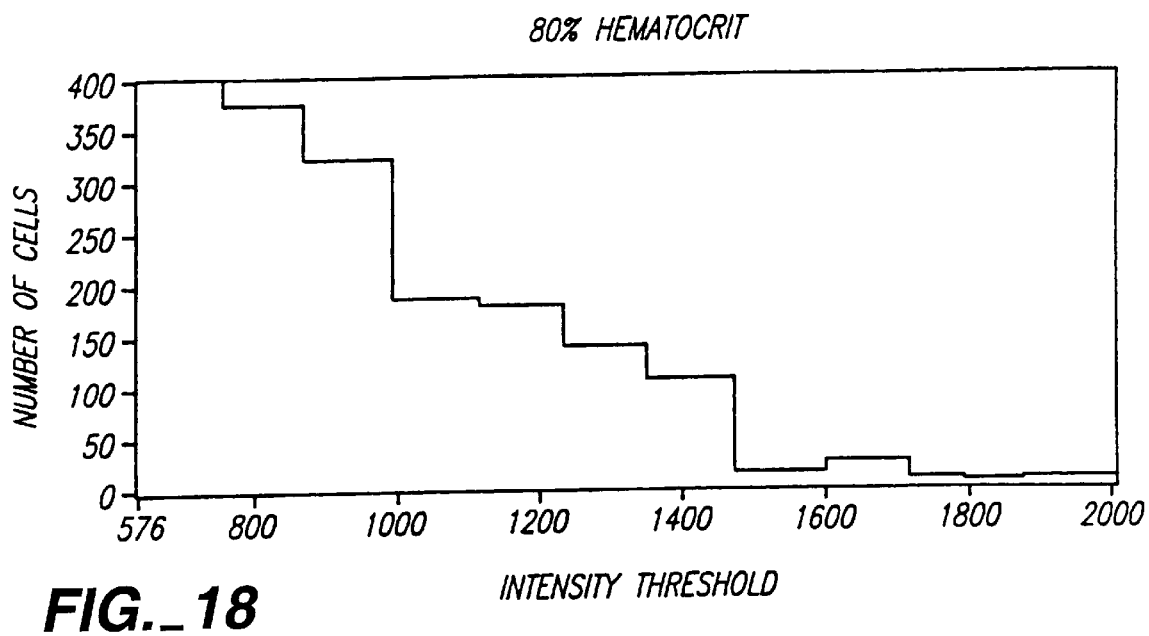
FIG._18
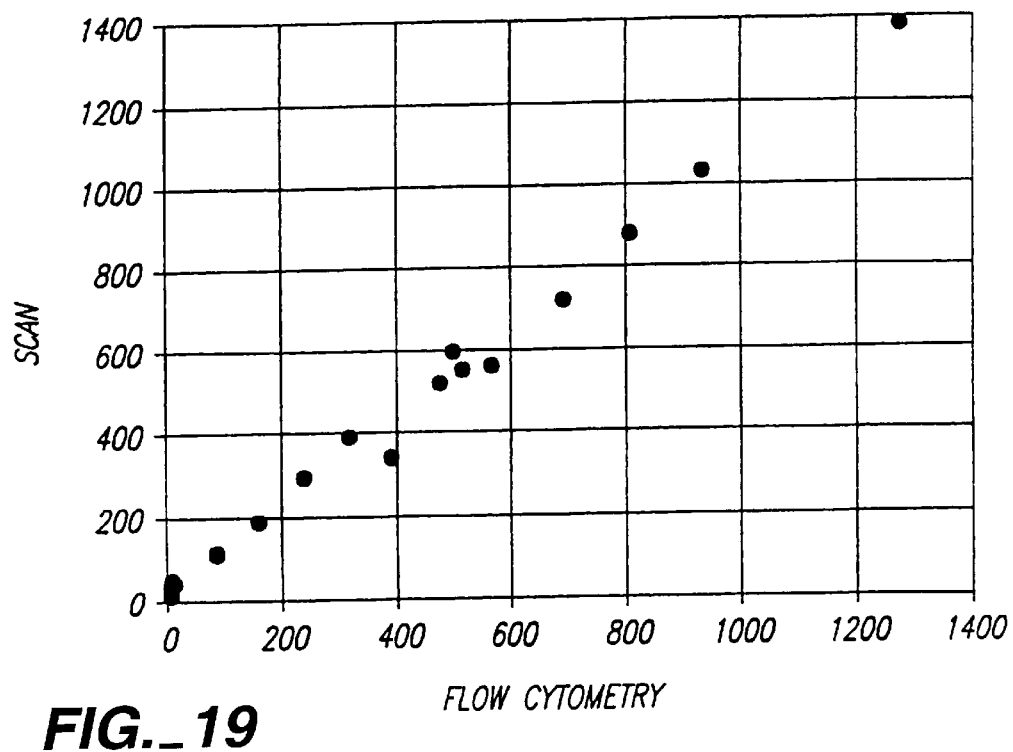
FIG._19

METHOD FOR PREPARING A SAMPLE IN A SCAN CAPILLARY FOR IMMUNOFLUORESCENT INTERROGATION

This application is a continuation of U.S. Ser. No. 08/328,241 filed Oct. 24, 1994 entitled METHOD FOR PREPARING A SAMPLE IN A SCAN CAPILLARY FOR IMMUNOFLUORESCENT INTERROGATION now U.S. Pat. No. 5,585,246 U.S. Ser. No. 08/328,241 is a continuation-in-part of Ser. No. 08/236,342 filed on May 19, 1994 now U.S. Pat. No. 5,547,849, which is a continuation-in-part of Ser. No. 08/018,762 filed on Feb. 17, 1993, now abandoned. Each of these applications are assigned to the assignee of the present application and are incorporated herein by reference.

BACKGROUND OF THE INVENTION

The present invention relates generally to the field of chemical and microbiological assay techniques and more specifically to a new and improved method of preparing a blood sample for cell classification and enumeration.

Since the beginning of immunological research, researchers have desired to be able to enumerate, identify and analyze specific particles in biological fluids. In particular, bodily fluids of mammalian patients are often analyzed to enumerate target cellular components. For example, blood may be analyzed to determine the absolute count of T-lymphocytes per unit of volume of whole blood that positively express the CD4 or CD8 surface antigens. A CD4/CD8 blood test is important to determine the progression of the human immunodeficiency virus (HIV) throughout different stages of development and particularly for the diagnosis of acute development of the viral infection to Acquired Immune Deficiency Syndrome (AIDS). The quantity of testing required for diagnosis of the AIDS virus alone is fueling the demand for simplified, efficient methods for cell enumeration.

To accomplish this objective, researchers have developed methods to mark specific cells with fluorescent markers that combine with a cell according to a specific cell traits or characteristics. Early immunologists used fluorescent dyes to stain the nucleus of white blood cells. The fluorescence from the dye or stain made it easier to enumerate and identify white blood cells. The breakthrough of monoclonal antibody technology soon permitted the conjugation of a monoclonal antibody with a fluorescent dye. This expanded the immunologist's ability to enumerate and classify cells according to their surface antigens.

The development of light detection devices capable of making highly accurate quantitative measurements of fluorescent intensity, a new potential for automated cell enumeration devices emerged. Flow cytometers were developed with fluorescent sensors to detect fluorescent emission. scanning devices were developed to scan microscope slides and automatically identify and enumerate target blood cells.

The development of such new instruments for automated fluorescent analysis has resulted in a demand for new and improved sample preparation and presentation techniques that simplify greatly cell enumeration without jeopardizing accuracy. The general purpose of such techniques is to expand analytical capabilities, improve reliability, simplify preparation, minimize handling of samples, and reduce the risk of disease transmission during sample handling.

Flow cytometers have the advantage of making rapid and accurate cell enumeration of different cells in a sample, but does not make direct accurate enumeration of cells per volume of whole blood. Flow cytometers present a sample of cells or particles before a light source in a linear flow path to measure the interaction of the laser with each cell or particle. The flow path consists of a downward flowing stream of liquid into which the cells are released one at a time into the center of the flow path.

The laser beam strikes each cell, causing the laser light to scatter in several directions. Light detectors are spatially oriented to detect such scatter. Fluorescent detectors can also be utilized to measure fluorescent emission from a cell. Statistical analysis of the data collected from the detectors can be used to characterize and enumerate the cells. The drawbacks of flow cytometry include undesirable consequences that relate to both how a sample is prepared and how the sample is presented. First, the flow cytometry instrument requires a sequence of sample preparation steps to remove red blood and plasma components and fluorescent markers. The steps often damage the cells, particularly unhealthy cells that are often brittle. The margin of error of the total sample preparation technique is compounded by each handling step or statistical enumeration technique. Moreover, many steps such as centrifugation, filtration, lysing, cell washing, etc. cannot be accomplished without defeating, to a large extent, the ability to absolutely count particulate as a function of absolute volume.

For example, a common method of preparing a sample of blood for enumeration and classification of the white blood cells in the sample includes the steps lysing red blood cells and centrifuging the sample to remove the excess red blood cell debris from the plasma. Lysation ideally will destroy all of the red blood cells, and none of the white blood cells. However, the ideal is difficult to accomplish and the effectiveness of lysation varies from patient to patient. For example some patients have delicate white blood cells. The lysing agents may damage the delicate white blood cells. Other patients, particularly patients with AIDS, produce red blood cells with a heightened resistance to lysing agents. Such samples require multiple applications of lysing agents, more effective lysing agents which cause a greater threat of damage to white blood cells that are the subject or target of the cell enumeration assay.

Centrifugation or gravitational separation is likewise an imperfect separation method. When centrifugation is used with lysation the white blood cells are mixed with the fluid while the lysed cellular debris is centrifuged to the bottom of the centrifugation vessel. Then, the white blood cells are decanted from the debris. Unfortunately, the centrifugal separation is not perfect and some of the unlysed particles will remain mixed with the cellular debris. Whenever separation techniques such as centrifugation and decantation are involved, the precise amount of target cell per unit of volume cannot accurately be measured because of the error introduced by the separation techniques. For example, when a known volume of blood is centrifuged after lysing the red blood cells, the debris from the lysed red blood cells settles to a sedimentary layer. Then, the plasma containing white blood cells is decanted from the debris. Regardless of the care taken, some of the white blood cells will remain in the cuvette with the debris from the lysed red blood cells. Consequently, a subsequent count of the white blood cells separated from the debris would not be an accurate count of the number of white blood cells which were contained in the original sample.

Red blood cells are lysed because the presence of red blood cells creates optical interference when fluorescence is used to detect and enumerate a targeted subclass of cells. Two types of interference make red blood cells troublesome.

First, red blood cells absorb light having a wavelength in the range of 200 nm to 500 nm. If laser light of fluorescent discharge occurs in this range, then the light that stimulates the fluorescent marker and the fluorescent discharge from the marker will be greatly weakened. Second, red blood cells and other plasma proteins autofluoresce These components of blood naturally contain fluorophores or molecules that discharge fluorescence when stimulated by light. Fluorescent markers must be chosen to have an energy of activation and an energy of fluorescent light discharged that likewise avoids autofluorescence of red blood cells.

Another drawback to flow cytometry techniques is that the sample is discharged from the nozzle in the form of atomized droplets, similar to a fine mist which can be carried through the air. Technicians using a flow cytometer may inhale or otherwise be exposed to the atomized particles. Should the sample be disease infected blood or other biohazardous material, then the technician is exposed to a risk of infection. Thus, there is a need for sample preparation methods to eliminate the risk of infection created by the release of these atomized particles.

Sample preparation for flow cytometers may include the use of fixatives or fixing agents which kill bacteria and viruses without damaging the physical structure of blood cells. Formaldehyde is a common fixative which may be added to the sample to destroy the infectious material. There are at least two drawbacks to the use of fixatives. First, fixing agents "kill the cell" without causing substantial damage to the physical structure. However, some morphological changes in the cell are caused by the fixative. Consequently, data from the fixed samples vary from data which would otherwise be obtained from untreated blood. Second, the addition of fixatives add a step of dilution. Each time a sample is mixed, handled, diluted, or centrifuged, a processing step is added to the overall procedure. The error of one step may not be significant alone; however, when the error is compounded with the error from each measurement step, the entire process may have a total undesirable margin of error. Consequently, the simplest possible assay technique with the fewest number of handling steps is advantageous to the researchers and practitioners that use fluorescent measurement devices because they make volumetric determinations more accurate.

Because volumetric enumeration (i.e., measurements of cells per unit of volume) is so important for diagnostic purposes, several attempts to make volumetric determination using a flow cytometer have been previously proposed. One common technique is to count all of the cells with a device such as a cell sorter to enumerate the total number of a certain subset of cells in a fixed volume of sample. Then, another sample is prepared that counts the number of target cells as a ratio of the cell type acting as a standard. Multiplying the ratio of target cells to standard cells by the number of standard cells per unit of volume gives a volumetric estimation of the number of target cells in a fixed volume. However, the margin of error from each cell enumeration is compounded together. The accuracy of volumetric cell counting devices can greatly be increased if the volumetric enumeration could be done in one measurement.

Another attempt to improve accuracy of volumetric cell enumeration for flow cytometry instruments entailed mixing a fixed number of fluorescent microparticles (e.g., beads) with a fixed volume of sample prior to the preparation techniques. Typically, the microparticles are labeled with the same fluorescent label as the cells targeted for enumeration. However, the concentration of markers on the microparticles is typically 5–10 times the intensity of the concentration of the labeled particles on the microparticles. A gate based upon the magnitude of fluorescent emission can be set to distinguish the microparticles from the target cells. Error is introduced into this technique when target cells have unusually high antibody concentration or when some of the microparticles have lowered fluorescent concentration. Even if the gating technique ensured that no microparticles would be confused with target particles, the technique requires two measurements to obtain one volumetric result. The error of the two measurement is compounded leaving the microparticle technique to be less accurate than a more direct technique that measures the number of cells per unit of volume in one measurement.

After the predetermined number of microparticles is mixed with the fixed volume of blood the sample is processed. During the processing step, some of the microparticles may be lost because the microparticles, which are typically made of polystyrene, have a density different from that of the target cells. Consequently, the sample is in continued need of mixing to ensure that the microparticles do not settle disproportionately.

Another known system for cell enumeration is fluorescent microscopy which combines fluorescent labeling with microscopy technology. Such systems include automated scanning microscopes to identify and enumerate subclasses of cells. Sample preparation includes smearing a microscope slide with a sample containing fluorescent stained or labeled blood cells (target cells). A light source is used to illuminate the cells against a grid in the background of the microscope optics. The number of cells per grid are counted and averaged to quantify the fluorescent stained cells. While this method can determine ratios of one cell type to another cell type, microscopic enumeration of smeared slides cannot determine directly the number of cells per unit of volume.

Furthermore, when manual cell counting is used, there is great opportunity for human error and fluctuations in accuracy from technician to technician. Automated techniques for counting cells smeared on a slide improves the ability to more accurately count the cells per unit of area across the slide, but methods of cell preparation that are compatible to the automated fluorescent microscopy cannot directly determine the number of target cells per unit of volume.

Beads likewise can be used with microscope slides to make volumetric enumeration of whole blood on a slide. One technique mixes substantially incompressible microparticles (e.g. beads) with a fixed volume of liquid sample before processing the sample and smearing on a slide. The ratio of target cells to microparticles times the number of microparticles per unit of volume can be used to estimate the number of target cells per unit of volume. However, this technique does not avoid the step of lysing. All of same problems of using microparticles with flow cytometry are equally applicable to the use of microparticles with fluorescent microscopy.

Consequently, there has arisen a need for a new and improved sample preparation and assay method that improves the accuracy and efficiency of volumetric cell enumeration and at the same time simplifies the preparation of the sample. Such a method would further be desirable if it eliminated separation and handling steps such as centrifugation, decantation, cell lysing, and cell washing. The assay would be especially beneficial if the volume of the sample could be preserved and accurately analyzed without need for microparticle additives or fixatives. The ability to analyze whole blood to make a precise volumetric cell identification and enumeration from either the entire sample or a portion of the sample would greatly expand and improve clinical and diagnostic applications of such assays techniques.

SUMMARY OF INVENTION

Briefly, and in general terms, the present invention comprises a new and improved assay for the enumeration of fluorescent stained target components of a whole blood sample by an imaging instrument. Similarly, the invention comprises a sample preparation prepared from whole blood. The whole blood sample is presented to the imaging instrument in a static state within a chamber, such that the blood cells and other particulate components of the blood, e.g., hematocrit, are evenly distributed throughout the chamber, such as a scan capillary. The sample preparation method ensures that the amount of target components per unit of volume of the whole blood is preserved by elimination of non-quantitative preparation steps. Moreover, techniques producing an even hematocrit layer are provided for optimum presentation of the target components to the imaging instrument. Typical target components include white blood cells that express certain surface antigens, such as CD-4 and CD-8 proteins.

An unexpected problem arises when attempting to image a static whole blood sample in a fixed volume chamber, such as a scan capillary. The static presentation of the sample induces an aggregation of red blood cells, or the so-called "Rouleaux effect." The Rouleaux effect causes a web of aggregated red blood cells throughout the sample, causing an uneven distribution of the hematocrit layer. This effect occurs rapidly in static blood but is reversible with agitation. Normally Rouleaux effect does not occur in rheological condition. The ultimate consequence of the Rouleaux effect is that cell detection by the imaging instrument is more difficult, if not impossible.

One advantage of the assay of the present invention is that it eliminates the Rouleaux effect. To inhibit aggregation of the red blood cells, a reagent is added to the whole blood sample which modifies the shape of the red blood cells, changes the surface properties of the red blood cells or modifies the environment, e.g., plasma, in which the red blood cells reside. Preferred reagents do not have fluorescent properties, do not lyse red blood cells, do not interfere with an antigen-antibody interaction, and may be reduced to a solid without causing chemical decomposition while effectively preventing cell aggregation.

Effective reagents include detergents that either alter the geometry of the red cells or alter the surface chemistry of the cells' surface proteins. For example, short chain alkyl zwitterionic compounds have been found to be effective. Similarly, the reagent may be a mildly hypotonic salt solution that geometrically alters the shape of the red blood cells. In addition, the PH of the sample may be altered to similarly affect the red blood cells. Alternatively, a quantitative amount of a simple diluent, such as an isotonic saline solution, may be added to the sample which apparently separates the hematocrit and reduces proteins concentration in the plasma sufficiently to prevent aggregation of the cells.

The blood sample prepared by the method of the present invention has a hematocrit layer substantially uniformly distributed throughout the scan capillary. Uniform distribution of white and red blood cells has several advantages. The advantage of having an even hematocrit layer is that a more even level of background noise from unbound fluorescent compound results. Since the fluorescent dye does not permeate the red blood cells, an even hematocrit layer is essential to having an even baseline layer. Having an even hematocrit layer ensures that the volume of plasma containing unbound fluorescent compound is evenly displaced throughout the scan capillary. This ensures that the quantity of unbound fluorescent compound will remain substantially constant throughout the scan capillary, maintaining a relatively even level of background fluorescence.

The first step of preparation is to obtain an aliquot of whole blood. The aliquot of whole blood is mixed and with a preselected amount of a fluorescent dye and ligand complex which tags the target particles. The complex for use in detecting lymphocytes expressing the CD-4 antigen is preferably a monoclonal antibody with a high affinity for the CD-4 antigen coupled to a reactive cyanine dye. The fluorescent dye is chosen such that absorption, autofluorescence and diffraction by red blood cells of the excitation light and emitted fluorescent light is minimized.

The preselected amount of fluorescent complex is chosen so that there is sufficient ligand or antibody to adequately bind to or accumulate on the target components. Excess dye and ligand are required to ensure sufficient tagging of the target particles in a reasonable amount of time. The excess fluorescent dye concentration in the sample, however, is selected to be sufficiently low, such that the fluorescence from target components produce an intensity response sufficient to be detected in the presence of the fluorescence produced by the unbound fluorescent dye. Likewise, the sample and fluorescent complex are allowed to incubate a sufficient amount of time to bind enough of the fluorescent complex to the target components to provide a fluorescent signal from the target components which will be distinguishable from the fluorescent signal from the unbound fluorescent complex in the sample. The incubation period is preferred to be sufficient to allow saturation of the fluorescent complex on the target components; however, saturation is not required. The resulting mixture allows the imaging instrument to detect peak intensities of fluorescence from the target components, thereby allowing the target components to be volumetrically enumerated with an improved level of accuracy and efficiency.

In the preferred embodiment, a quantitative amount of reagent to inhibit the aggregation of red blood cells is added to the aliquot of the whole blood sample and fluorescent dye-ligand complex mixture. Alternatively, the reagent may be added to the whole blood sample prior to adding the fluorescent complex. Likewise, the reagent may be mixed with the fluorescent complex and both added to the whole blood sample together. The blood sample, fluorescent complex and reagent mixture is delivered into a chamber for interrogation by the imaging instrument. The mixture may be placed into the chamber after incubation of the fluorescent complex or the mixture may incubate in the chamber.

The preferred chamber for interrogation by the imaging instrument is a scan capillary which typically is made of glass or plastics. The length and width of the scan capillary defines a generally horizontal scanning plane over which the imaging instrument interrogates the sample on a pixel-by-pixel basis. The imaging instrument uses a laser light source that is focused onto the scan capillary to illuminate a cylindrical region perpendicular to the scanning plane having a cross sectional diameter defining a scan spot. The imaging instrument excites the fluorescent complex and detects the fluorescent emission of the unbound complex and that bound to the target components. The volume of the sample analyzed is equal to the cross sectional area of the lumen of the capillary times the length of the capillary that is scanned by the imaging instrument.

The use of such an imaging instrument in conjunction with the scan capillary has the further advantage that the blood sample, which may be contaminated with infectious viruses or bacteria, never contacts the permanent parts of the imaging instrument. Because the blood sample is contained within the scan capillary there are no atomized particles which may be carried off into the air. Consequently, fixatives are not required. Thus, the method of the present invention provides for the safe effective analysis of whole blood.

In summary, the method of the present invention includes the steps of mixing a select amount of fluorescent complex with whole blood, incubating the mixture for a period of time, adding a reagent to inhibit aggregation and drawing an aliquot of the mixture into a scan capillary. The sequence of the steps is not critical to the desired result. The lumen of the scan capillary is interrogated by an imaging instrument that illuminates a columnar region along a scan path and periodically measures the fluorescent response from the column. The method further improves cell enumeration accuracy by simplifying the sample preparation techniques by avoiding error caused by multiple processing steps, such as lysing, washing out excess antibody, and centrifugation of the sample. Furthermore, the prepared sample is contained by a scan capillary and never touches the working parts of the imaging instrument. Consequently, whole blood assays need not be treated with a fixative to kill infectious bacteria and viruses in the sample. These and other features and advantages of the present invention will become apparent from the following more detailed description, when taken in conjunction with the accompanying drawings which illustrate, by way of example, the principles of the present invention.

BRIEF DESCRIPTION OF THE DRAWING

FIG. 1 is a perspective view, partially cut away of a scan capillary containing a sample of whole blood.

FIG. 1A is an enlarged fragmentary view of FIG. 1 taken in the area defined by 1A of FIG. 1.

FIG. 2 is a diagrammatic representation of a fragmentary portion of the scan capillary of FIG. 1 intersected by a beam of laser light to define an illuminated column within the capillary.

FIGS. 3A–E are elevational views of various illuminated pixels above a bar graph representation of corresponding fluorescent responses.

FIG. 4A is graphical illustration of fluorescence detected along a single scan line across a sample with an even hematocrit layer.

FIG. 4B is a graphical illustration of fluorescence detected along a single scan line across a sample with an even hematocrit layer.

FIG. 5 is an enlarged illustration of a plurality of red blood cells stacked together per the Rouleaux effect.

FIG. 6A is a transverse cross-sectional view of the scan capillary of FIG. 1 having three target cells with an uneven hematocrit.

FIG. 6B is a graphical illustration of the fluorescent signal produced by a transverse scan line over the sample of FIG. 6A.

FIG. 7 is an illustration of light waves contacting a red blood cell.

FIG. 8 is the absorption spectrum of red blood cells in the range of light with a wavelength of 250 to 900 nm.

FIG. 9 is a graphic illustration of the intensity of red blood cell autofluorescence for various wavelengths of excitation light.

FIG. 10 is a kinetic diagram illustrating binding kinetics for fast and slow antibody/antigen binding reactions.

FIG. 11 is a histogram illustrating average peak height from cells labeled with "CY5" conjugated CD4 after set times of incubation.

FIGS. 12–14 are scatter plots of samples respectively prepared by the steps outlined in Examples 1 through 3

FIGS. 15–18 are histograms comparing the number of cells that have fluorescent intensities at various peak levels.

FIG. 19 compares a number of cell counts from several patients to compare the effectiveness of samples prepared by the present invention and interrogated by an imaging instrument and samples prepared for and interrogated by a flow cytometer.

DESCRIPTION OF THE PREFERRED EMBODIMENTS

The assay of the present invention prepares and presents a sample of biological fluid, such as human whole blood, in a scan capillary. The biological fluid has a liquid phase, such as plasma, and a solid phase comprising particulate, like blood cells and platelet, of various types and subclasses. FIG. 1 is a perspective view of a scan capillary 10 having a lumen with a floor. The capillary contains a fixed volume of sample 12. The sample consists of fluid 14 and particulate 16. The sample in a scan capillary is presented for interrogation by an imaging instrument that scans a planar region called a scanning plane parallel to the lumen floor of the capillary.

With reference to FIG. 1A, the labeled particles 22 and 24 are respectively suspended in the particulate layer or the fluid layer. The target components 22 and 24 are a subclass of particles that are labeled with a fluorescent markers. For example subclass of blood cells may be white blood cells, platelet or various subsets of white blood cells such as lymphocytes or even subclasses of different lymphocytes. Target components of other biological fluids may be bacterium, virus, protozoa, or parasites. The fluorescent markers are chosen to bind specifically with cells according to a cellular trait, for example the expression of a population of specific surface antigens. A fluorescent marker that is effective at binding to a specific type of surface antigen can made by conjugating a monoclonal antibody that binds specifically with a type of surface antigen to a fluorescent dye. Fluorescent markers in the sample may be unbound in the whole blood sample or accumulated on or within a target cell.

The method of the preferred embodiment is suitable for use with an imaging instrument scanner of the type disclosed in co-pending U.S. application Ser. No. 08/236,645 filed May 2, 1994, now U.S. Pat. No. 5,556,764 which is incorporated herein by reference. While the imaging instrument is compatible with the subject method of the present invention, reference to the instrument is made by way of example, and not by way of limitation. Such an imaging instrument having an object lens 50, narrows a beam of laser light 34 in the form of a gausian waist that intersects the scan capillary as shown in FIG. 2. The gaussian waist illuminates a columnar region 56 in the scan capillary 10 that equals the diameter 58 of the gaussian waist times the depth 60 of the lumen of the column. As the illuminated columnar region passes through the capillary, it excites fluorescent matter, such as a target in its path. The fluorescence 64 from the columnar region can be detected by a light detector to produce a fluorescent signal which is sampled periodically by a digital sampler into a series of digital data samples.

Each digital data sample corresponds to the amount of fluorescence emitted from the illuminated column at the time of sampling. The area representing the location of the illuminated column at the time of sampling is called the pixel region. Each pixel region is a snapshot of the illuminated column corresponding to each digital data sample.

The rate of sampling is coordinated with the speed that the laser travels across the sample so that the pixel region represented by each data point overlaps with pixel regions corresponding to prior and consecutive data points.

When a target cell 80 is located within a pixel region the corresponding data point reflects an increased fluorescent measurement. The increased fluorescent measurements can be mathematically detected as peaks. The peaks can be enumerated to determine the number of target cells in the fixed volume capillary. Consequently the sample must be prepared to facilitate the accurate detection of target particles within a biological fluid.

The method of the present invention for preparing and presenting a sample can be illustrated with reference to preparing a whole blood sample for enumeration of subclasses of white blood cells that express particular surface antigens. The particular class of blood cells that is the target of the cell enumeration will be referred to as the target cell and the particular surface antigen that identifies the target cell will be referred to as the target antigen.

The method of a preferred embodiment begins with the step of selecting a fluorescent marker by choosing a fluorescent compound, such as dye or other fluorophore, that can be conjugated to a monoclonal antibody or similar ligand that has a wavelength of excitation and a wavelength of emission that minimizes optical interference such as light absorption, autofluorescence and scatter from the red blood cells in the sample. The benefit of choosing such a dye allows the sample to be prepared without having to lyse the red blood cells, which in turn permits a more accurate volumetric count of particles.

Another step of a preferred embodiment is to carefully choose the amount of fluorescent marker used in the assay. Since the purpose of the assay is to preserve the volume of the whole blood throughout the steps of preparing a sample and to manipulate the whole blood as little as possible, the excess unbound markers cannot be washed from the cells. Consequently, the amount of fluorescent marker selected must be great enough that the fluorescent markers will be able to bind to target cells in sufficient quantities that will make the cells detectable. On the other hand, the concentration must be low enough that the fluorescence and signal caused by the unbound fluorescent compound does not drown out the fluorescent signal from the cell. The concentration of the fluorescent compound in the solution multiplied by the volume displacement of the cell must be significantly less than the number of fluorescent markers bound to the cell.

The predetermined amount of fluorescent marker comprising a fluorescent dye conjugated to monoclonal antibodies can be mixed with a volume of whole blood. In one preferred embodiment, the fluorescent markers may be added in a fixed volume of liquid to a known volume of blood to preserve the ability to make volumetric determination of target cells in the blood. An alternative way of adding the fluorescent markers to the blood involves evaporating the fluorescent markers to a film in a mixing vessel before adding the whole blood. The use of a dried fluorescent marker allows the blood to maintain substantially the same volume when mixed with the fluorescent markers. When the fluorescent markers are combined with blood in a dried form, it is desirable to add a like amount of sugar to the liquid solution of fluorescent markers before evaporation. When evaporated, the dye-antibody complex and the sugar form a matrix that is more easily dissolved by blood plasma.

After the sample is combined with the fluorescent marker, it must be incubated for a period of time prior to scanning the scan capillary by the imaging instrument. The incubation occurs before the sample is placed in the scan capillary in one embodiment of the invention, but alternatively may occur in whole or in part while the sample is in the scan capillary. When the blood sample is drawn into a capillary, the blood cells are drawn evenly throughout the length of the capillary where evaporation or meniscus effect may occur during filling. The forward extremity is the end of the capillary toward which the sample is drawn. A method of the preferred embodiment compensates for this variation by scanning the entire length of this column except the forward extremity of the scan capillary. Also, there maybe some uneven distribution of the cells along the edges of the capillary.

Quantification of cell subsets can be accomplished in several ways. One way is to use a chamber of known volume or cross-sectional area and introduce blood that has been stained but not significantly diluted. All or part of the chamber can then be interrogated. The number of fluorescent events counted can be divided by the volume of the chamber interrogated to arrive at the events per unit volume of blood. If a quantitative dilution is performed on the blood and a known volume chamber is used then the events per unit volume is divided by the dilution factor to derive the events per unit volume of blood. If the volume of the chamber or length of the scan is not known then indirect techniques such as adding a known number of microparticles, such as beads, to the sample or quantifying the level of background fluorescence can be used to determine volume scanned. These methods are less desirable but can be done effectively if care is taken with this assay method. If only the ratio of two or more cellular events is required, not the absolute count, then quantifying the dilution or knowing the precise volume of the scan capillary may not be important. In this case the advantages of this assay will mainly be to reduce sample handling and potential contamination, eliminate the need for lysing and improve detection by smoothing out the hematocrit layer. Other schemes to obtain cellular event information using this assay by those skilled in the art, these are meant only to be examples of several methods.

The assay of the present invention also includes the addition of a reagent or other additive to prevent red blood cell aggregation and to create a smooth layer of hematocrit across the floor of the scan capillary. One type of reagent is diluent such as an isotonic saline solution that serves to overcome the adhesive force that contributes to cell aggregation. Other treatments for cell aggregation involve altering the pH from physiological conditions, adding a hypotonic solution, adding a detergent that alters the shape of the cell or changes the surface chemistry of the cell. The purpose of the step of adding a reagent is to create an even hematocyte layer throughout the capillary.

The need for an even hematocrit layer in the sample arises from the relationship between the hematocrit layer and the background noise. To more fully understand this relationship, please refer to FIG. 3 depicting five pixels or scan columns of a fixed diameter and depth. Each pixel contains some plasma with unbound fluorescent markers. Each pixel region illustrated contains different amounts of marked (target) and unmarked cells. Each scan column will produce different levels of fluorescent intensity.

Pixel A of FIG. 3 contains no cellular material, but only contains plasma 82 with a fixed amount of dissolved fluorescent markers 84. The measured fluorescent response from the light is represented by bar 90 on the bar graph above. Pixel B contains unlabeled cells 86 that displace half of the plasma in the pixel. When stimulated by the laser light source, the fluorescent response from Pixel B will be approximately one half of the fluorescent response from Pixel A. The corresponding response from Pixel B is represented by bar 92 on the bar chart below Pixel B. A comparison of Pixel A and Pixel B shows that the displacement of plasma containing fluorescent markers by red blood cells contains a proportionate reduction in the amount of fluorescence.

Pixel C represents a column packed with red blood cells 86, such that substantially all of the red blood cells displace the unbound fluorescent markers 84 dissolved in the plasma 82. Consequently, only a small amount of fluorescent emission is detected in Pixel C. An appropriate fluorescent response is illustrated by the corresponding bar 94 in the bar chart below Pixel C. Thus, the principle of displacement illustrates the effect on a background fluorescence due to uneven levels of hematocrit. The background fluorescence will increase when fewer unmarked cells are in the pixel and will decrease when there are more unmarked cells in the pixel.

Pixel D contains unmarked cells 86 that displace about one half of the plasma 82. Furthermore, the pixel contains a target cell 88 that is labeled with fluorescent tagged antibodies. The amount of fluorescent response caused by the unbound fluorescent markers is represented by the lower portion 96 of the corresponding bar 100 in the bar chart below Pixel D. The lower portion 96 corresponding to the background fluorescent response from the unbound antibodies is about equal to the bar 92 representing the background fluorescence from substantially the same amount of unbound antibodies in Pixel B. The portion of the fluorescent response caused by the target cell labeled with fluorescent markers is represented by the upper portion 98 of the corresponding bar 100. As shown, and what would be typical for a lymphocyte expressing the CD4 antigen, the background fluorescence is about the same as that for the target cell. The total fluorescence resulting from the cell and the unbound antibodies is additive.

Pixel E contains packed cells 86 similar to Pixel C. However, Pixel E contains a target cell 88 labeled with fluorescent markers and located at the bottom of the pixel. The amount of fluorescent markers affixed to the target cell is equal to the amount of fluorescent markers affixed to the target cell contained in pixel D. The fluorescent response from the unbound markers is represented by the lower portion 102 of bar 106. The magnitude of the lower portion 102 of bar 106 is similar to the magnitude of bar 94 corresponding to Pixel D. The fluorescent response from the target cell is represented by the upper portion 104 of bar 106 and is somewhat smaller than the upper portion 98 of bar 100 representing the fluorescent response from the target cell in Pixel D due to same scattering and absorption by the additional unbound cells 86.

As shown in FIG. 3, the fluorescent response caused from a particular pixel region is additive of the quantity of fluorescent marker that is contained in the pixel region. This principle is based upon the assumption that the entire pixel or scan column is stimulated by light. The total measured fluorescent response may be somewhat diminished due to absorption or diffraction of the stimulated fluorescent markers by the red blood cells in the pixel. The above illustration teaches the importance of an even distribution of hematocrit to obtaining an even baseline. Typically, the hematocrit layer displaces fifty percent of the volume of whole blood. Therefore, a fluctuation in the distribution of hematocrit along the length of the capillary by fifty percent will have a corresponding change in the fluctuation of the background fluorescence from pixel to pixel. When the background fluorescent changes substantially, small peaks from target cells with low antigen density may be rendered undetectable.

Reference is made to FIG. 4A, a graphical representation of the digital data values in a single scan line prepared according to the method of Example 1 below. A scan line is represented by the data points generated as the illuminated column makes one traverse of the width of the scan capillary. The baseline 110 is caused by a sample that has an even hematocrit layer. A peak 108 appears that has a height above the baseline equal to approximately one half of the background signal. Such a signal height is typical of a peak detected from, certain lymphocytes, such as a so-called B-cell. The peak whose height over the background is only a fraction of the intensity of the background because peak height is more than five times the maximum fluctuation in the baseline 110. The maximum fluctuation is defined as the highest value along a scan line that is not detected as a peak minus the lowest value of the baseline.

FIG. 4B represents the data points corresponding to pixels along a scan line. The sample is prepared according the steps outlined in Example 2 herein. No step has been taken to eliminate cell aggregation. Consequently, the scan line is uneven. Virtually any peak that is similar in size to peak 108 would be indistinguishable from the baseline. For example, data point 112 on scan line 113 in FIG. 4B is approximately the same size as the peak 108. Thus it would be difficult if not impossible for an imaging instrument to determine whether the data point is a peak value from a target component or a fluctuation in the background fluorescence.

An uneven background signal is particularly troublesome when cell aggregation occurs. Cell aggregation is a physical characteristic of blood cells and causes an uneven distribution of the blood cells throughout the hematocrit layer. The red blood cells have outer membranes or surfaces that are made of surface molecules that tend to adhere to other surface molecules on other red blood cells. The tendency of the cells to aggregate is facilitated by the biconcave shape of the disk. FIG. 5 illustrates the relationship between the shape of a red blood cell and cell aggregation or the Rouleaux effect. Red blood cells have the shape of bi-concave disks. When the red blood cells are oriented in an end to end manner similar to a stack of tires, a relatively large amount of cell surface contact occurs between the cells. The combination of the adhesive attractive force between the red blood cells and the unique bi-concave shape is what causes the Rouleaux effect. End to end stacking of red blood cells is illustrated by row 150 of red blood cells. Cell stacking does not exclusively occur in an end to end manner. Sometimes, the concave portion of the disk will stick to the circumference of one or more neighboring cells that are stacked together. Cell 152 is affixed to cells 153, 154, and 155.

The various ways that red blood cells orient themselves according to the Rouleaux effect creates a web of stacked cells throughout a static blood sample. A static condition of the sample favors cell aggregation. The kinetic energy of cells in motion is often sufficient to overcome relatively weak the adhesive forces that cause the Rouleaux effect. Consequently, the Rouleaux effect is not, a concern in Theological methods of cell analysis such as flow cytometry, but is a significant concern with a morphological technique as is characteristic of the present invention. The Rouleaux effect is not the same as blood coagulation or clotting. The binding force is not caused by covalent binding of cell matter and is reversible by sample mixing.

The Rouleaux effect defeats the goal of a substantially constant background fluorescence which in turn adversely affects the ability of the imaging instrument to detect cells. Cells are detectable because the concentration of fluorescent markers bound to the cell causes a heightened fluorescent emission over the baseline. Red blood cells displace the amount of fluorescent matter in the capillary. When the displacement is uneven and greatly fluctuates from pixel to pixel, an erratic and uneven baseline will result. Conversely, presenting a sample in a manner whereby the hematocrit layer is uniformly distributed throughout the sample minimizes the fluctuations in the baseline. As a result more peaks are detectable.

FIG. 6B shows a graphical representation of the fluorescent response from a scan line that scans across a scan capillary 10 containing unevenly distributed cells 118. FIG. 6A shows a corresponding sample where the number of red blood cells 86 are not evenly distributed due to the Rouleaux effect. The sample is sectioned along the scan line to illustrate what causes the pattern on the graph in FIG. 6A. The scanning column detects three marked cells 120, 122, and 124 along the scan line 131. As the laser beam scans across the sample, the background signal drops when the laser beam encounters a row or clump of red blood cells. This is primarily caused by the fact that the clump of stacked cells displace a large amount of plasma. Consequently, fewer unbound fluorescent markers are present in that particular pixel.

Other locations along the scan line 131 have fewer red blood cells 86. At such locations less plasma is displaced causing a larger number of antibodies to be contained within the cell and a higher background signal. Since the Rouleaux effect causes a pattern of stacked cells followed by areas with no cells, the baseline signal of a sample with the Rouleaux effect is erratic or noisy. When cells labeled with a concentrated amount of fluorescent markers are present in a sample, they are often hidden in the background noise. For example, cell 120 is located in an area where there are no red blood cells. Consequently; the cells peak 126 is elevated by the relatively high number of fluorescent markers in solution. A target cell 122 that is found within a clump of stacked cells produces a peak 128 of equal height. Because the cell 122 is surrounded by packed cells, the peak is difficult to detect. Likewise, when a cell 124 is between an area of stacked cells and an area without cells, the corresponding peak 130 is most difficult to detect.

The Rouleaux effect can be treated by altering the adhesive property of the surface molecules or by changing the disk-like shape of the red blood cells 86. One way of reducing the adhesive forces between respective surfaces of the red blood cells is to add a diluent, such as an isotonic saline solution. It is believed that the composition of the blood plasma contributes to the adhesive forces between the molecules. By attenuating the blood plasma with a diluent, the adhesive properties of the cells are reduced and a more even hematocyte layer is obtained. In a preferred embodiment, one hundred microliters of blood is diluted with one hundred seventy-five microliter of Isotonic saline diluent and found to effectively reduce the Rouleaux effect. A dilution ratio of 1:1 whole blood to isotonic saline diluent has been shown to be effective. A dilution ratio of 4:1 whole blood to diluent was shown to have the effect of eliminating cell aggregation.

The Rouleaux effect is, at least in part, result of the disk like shape of the cells. Consequently, any reagent or additive, such as a detergent that changes the shape of the cell will serve to eliminate the Rouleaux effect. One possible method is to add a buffer solution that alters the pH in either direction from the physiological conditions. A small change in the pH will effectively alter the shape of the cell without causing significant lysing of the red blood cells. If, however, the solution is incubated for an extended period of time, the cells will eventually burst. An ideal way of changing the pH of the solution is to add a mild solution of HCl or NaOH. A mildly hypotonic solution also has the effect of altering the shape of red blood cells by changing the osmotic pressure of the red blood cells in solution. Like buffered treatments for Rouleaux effect, the use of hypotonic solutions will cause some lysing of red blood cells eventually.

Some detergents have been discovered to effectively prevent the Rouleaux effect. The use of detergents have advantages over the use of hypotonic solutions, isotonic diluents, and buffered solutions. Detergents can be evaporated to form a solid and mixed with the sample. Dried additives do not dilute the whole blood and improve the volumetric enumeration of red blood cells. Any detergent additive that reduces the adhesive effect caused by the iteration of surface molecules of red blood cells or changes the shape of the red blood cells is acceptable if the compound 1) does not change the antibody/antigen reaction on white blood cells, 2) does not cause significant amount of red blood cell lysis, 3) does not autofluoresce, and 4) can be evaporated to a dried form.

Zwitterionic detergents and particularly short chain zwitterionic detergents are effective treating the Rouleaux effect. By way of example, n-Octyl-N,N-dimethyl-3-aminio-1-propanesulfonate marketed under the trademark "ZWITTERGENT 3-08" by CALBIOCHEM, Inc., California. was found to be effective at treating the Rouleaux effect and had minimum effect of lysing red blood cells. Other longer chain alklyl zwitterionic compounds effectively treated the Rouleaux effect, but tended to cause more lysation of red blood cells. Long chain zwitterionic compounds include n-Decyl-N,N-dimethyl-3-amonio-1-propanesulfonate marketed under the trademark "ZWITTERGENT 3-10"; n-dodecyl-N,N-dimethyl-3-amonio-1-propanesulfonate marketed under the trademark "ZWITTERGENT 3-12"; and n-tetradecyl-N,N-dimethyl-3-amonio-1-propanesulfonate marketed under the trademark "ZWITTERGENT 3-14".

The "Zwittergent" compounds may be added to the fluorescent markers prior to evaporation. It may be added in solid form before or after the fluorescent markers are mixed with whole blood depending upon the purpose and requirements of the sample preparation technique. Sufficient detergent should be added to the whole blood to make a ten to one hundred millimolar solution of detergent in whole blood. A preferred embodiment adds sufficient detergent to make a thirty millimolar solution of detergent in whole blood. Other common detergents may be used. By way of example some detergents found to be acceptable includes polysorbate 20; polyoxyethylene (20) sorbitan monolaurate which can be urchased under the trademark "TWEEN" from Pierce Chemical, Rockford, Ill. A non-ionic detergent that is found to be effective in treating the Rouleaux effect is polyethylene glycol-p-isooctylphenlyether; octylphenooxypolyethoxyethanol which can be purchased under the "TRITON X-100" trademark from Pierce Chemical, Rockford, Ill.

The goal of volumetric enumeration of blood is substantially furthered when processing steps that destroy the ratio of particulate to volume are eliminated from the sample preparation technique. For example, if a sample is centrifuged to separate particulate from liquid, the technique cannot always ensure that the particulate that is separated from the liquid represents the entire amount of particulate that was present in the original volume. Consequently, volumetric analysis is difficult when separation steps or unnecessary handling of the sample is required.

One of the most difficult problems with preserving a fixed volume in assays that analyze fluorescent marked particles is the optical interference caused by the red blood cells in the form of signal absorption, signal diffusion or diffraction, and auto fluorescence. FIG. 7 is an illustration of light intersecting with a red blood cell 142. While most of the light waves 140 pass through the red blood cell, waves 144 are absorbed and waves 146 are scattered. Wave 148 illustrates light produced by the autofluorescence of the red blood cell.

Red blood cells absorb significant amount of light hen exposed to white light. FIG. 8 illustrates the amount of light absorbed from red blood cells at different wavelengths. The vertical axis represents the intensity of the absorption. The horizontal axis represents the different wavelengths of light. As the graph indicates, most light between the wavelengths of two hundred and five hundred nanometers is absorbed by the red blood cells. For the purpose of scanning a sample of whole blood without removing the red blood cells, laser light having a wavelength above five hundred and fifty nanometers should be used. Thus, excitation light having a wavelength over five hundred and fifty nanometers, which includes the red Helium Neon (HeNe) laser at six hundred thirty-three nanometers, is a preferred light source. Diode lasers would likewise be acceptable, especially those emitting light with a wavelength of approximately seven hundred nanometers (nm).

Red blood cells also produce autofluorescence. FIG. 9 is a graphic representation of the autofluorescence of red blood cells at different wavelengths of excitation. Autofluorescence is at a peak at wavelengths of 310 nm, 500 nm and 630 nm. However, the amount of autofluoresence above 500 nm, when compared to the intensity of background fluorescence and fluorescence from a tagged target component, is small enough that it is not a significant barrier to detection of target components by the imaging instrument.

Another type of optical interference is diffraction or scatter. When light hits an object a certain amount of light will be diffracted off the surface of the cell rather than pass through the cell. Consequently, red blood cells will weaken the intensity of the laser light source or the fluorescent discharge from the fluorescent markers. Unlike absorption and autofluorescence, diffraction is not significantly dependant upon the wavelength of the light it diffracts.

In keeping with attempts to minimize the amount of optical interference in an assay, fluorescent dyes may be selected to be activated by a light source having a wavelength above 550 nanometers. A red HeNe laser produces a peak wavelength at about 633 nanometers and is found to effectively excite a whole blood sample without debilitating levels of optical interference. Similarly, dyes must be selected to be activated by red HeNe light and produce peak fluorescent wavelengths preferably above 550 nanometers. Dyes from the cyanine family have been found to meet this criteria. "CY5" and "CY5.5" are dyes from the cyanine family and are effective for use with a red HeNe laser. They are both available under those brandnames from Biological Detection Systems, Inc., of Pittsburgh, Pa. "CY5" has a peak emission with a wavelength of 667 nanometers and an emission spectrum ranging from about 630 nanometers to 800 nanometers. "CY5.5" has a peak emission with a wavelength of 695 nanometers and an emission spectrum ranging from about 650 nanometers to 780 nanometers. Since the majority of the fluorescent emission from the dye are above 550 nm, the light emitted from the fluorescent complex is not absorbed significantly by the red blood cells.

The choice of a laser light source and dye type is important to the overall objective of creating a method for preparing a sample for volumetric determination. Elimination of optical interference such as absorbance means that the red blood cells do not have to be lysed. Elimination of lysing removes a problematic step that hinders volumetric enumeration of a sample.

With reference to FIG. 2, the illuminated column 56 is defined by the diameter 58 of the gausian waist. The depth 60 of the column corresponds to the inner dimensions of the scan capillary 10 which preferably has a lumen 62 having a rectangular cross section that is constant along the length of the capillary. The depth of the scan capillary lumen measured at an angle perpendicular to the scanning plane defines the column depth.

The preferred depth of the scan capillary lumen 62 depends upon the particular assay. The minimum depth of the capillary corresponds to the size of the target cells or other particulate in a sample. This is to ensure that the inlet of the scan capillary is not clogged by the cells in a sample. Such clogging is likely to occur in a capillary that has a lumen depth relatively the same size as the diameter of a blood cell. Clogging of the capillary causes an uneven hematocrit which defeats the purpose of the volumetric analysis. consequently, capillaries with a lumen depth of more than ten microns is preferred for use with whole blood.

The upper limit of the depth of a scan capillary is determined by the diminished signal due to optical interference or the ability of the laser 34 to penetrate the sample and the ability of the fluorescence to be transmitted through the blood cells. Experimentation has shown that the ideal depth of the capillary depends upon the depth of the hematocrit layer. The thinner is the hematocrit layer, the less optical interference will result from the red blood cells. However, the thicker is the hematocrit layer, then the larger volume of blood can be scanned in one sample. Therefore, if the sample is diluted, the ideal capillary width may be increased proportionally.

Experimental data has shown that a hematocrit layer of above one hundred microns is substantially impenetrable by a red HeNe laser with a wavelength of 633 nanometers. A hematocrit layer of between fifteen to thirty microns can be interrogated with little difficulty. A hematocrit of less than fifteen microns causes deminimis levels of optical interference. Since the hematocrit layer typically occupies about one half of the volume of whole blood, a preferred scan capillary depth for whole blood is about thirty to sixty microns. When applying these same considerations to blood diluted by a factor of approximately 1:3 blood to diluent, a scan capillary with a depth of one hundred to two hundred microns is acceptable.

The ideal depth of the scan capillary may depend on the blood sample concentration of the unbound dye and/or fluorescent markers, such as antibody-dye conjugates. Capillary depth and unbound fluorescent marker concentration must be balanced so that the fluorescence from the tagged target cells can be detected over the background fluorescence caused by unbound fluorescent markers in the sample. Background fluorescence is the fluorescent emission from unbound fluorescent markers. The fluorescent markers remain unbound in the solution and are excited by the laser beam to produce a fluorescent emission. The presence of an excessive amount of unbound markers may interfere with the cell enumeration. Removal of the unbound antibodies from the cellular material can only be accomplished by separation techniques that may include gravitational separation or cell washing. Such separation steps may also remove target components and reduce the accuracy of the volumetric cell enumeration.

It is therefore desirable to provide a cell enumeration technique that preserves the original volume by eliminating separation techniques that remove the unbound antibodies from the cells. By doing so, a more accurate count of cells in a given volume of whole blood can be made. The trade off is that unbound antibodies must remain in the solution. Consequently, it is important to choose an antibody concentration that allows the cells to be detectable over the background noise.

The precise amount of antibody to produce optimum results must be determined by trial and error. In most cases a mass of antibody ranging between 0.1 to 25.0 micrograms will combine with one milliliter of blood to effectively label the target cells without causing excess interference. In a preferred embodiment, anywhere between 0.5 to 5.0 micrograms of anti-CD3, anti-CD4, or anti-CD8 antibodies labeled with "CY5" or "CY5.5" dye will be an effective amount of fluorescent marker to label a one milliliter sample of blood without drowning out the signal from the fluorescently marked cells.

The concentration of fluorescent marker that will produce optimum result will depend primarily on two factors, column depth and concentration of markers on target cells. The larger the depth of the column, the less fluorescent markers should be used. When a cell has a high concentration of fluorescent markers per unit of displaced volume of cell, a higher concentration of fluorescent markers can be tolerated.

FIG. 3 illustrates how a cell is detected over the background fluorescence. Pixel D, as illustrated contains approximately 50% plasma by volume and a target white blood cell. The fluorescent response from the background in Pixel D will be the same as in Pixel B which contains approximately 50% plasma by volume but does not contain a target white blood cell. The difference in the magnitude of the total fluorescent emission from Pixel D and the total fluorescent emission from Pixel B can be attributed to the concentration of fluorescent markers on or in a target cell. This concentration can be expressed in terms of the number of antibodies bound to a target cell divided by the displacement or volume of the cell. The markers may bind to the cells in several ways including the binding of fluorescent tagged antibodies to surface antigens of a cell. Other fluorescent markers may be transported through the cell membrane and accumulate on the Deoxyribonucleic Acid (DNA) and Ribonucleic Acid (RNA) strands.

The concentration of fluorescent markers that bind to a cell is dependent on several factors including the number of sites that a fluorescent marker can bind to. For example, a CD4 positive helper T-lymphocyte will have approximately 50,000 antigens on its surface to which fluorescently labeled anti-CD4 monoclonal antibodies can possibly bind. On the other hand, the amount of DNA in a cell can potentially provide in the order of a billion binding sites for certain dye molecules.

To understand the number of binding sites for fluorescent conjugated monoclonal antibodies it must be understood that monoclonal antibodies bind to specific antigens on the surface of a target cell which may be defined as target antigens. The number of target antigens is not the same as the total number of antigens on a cell. A cell may have hundreds of different types of antigens on the surface and only the population of target antigens affects the number of fluorescent labeled monoclonal antibodies on the surface of a cell.

The concentration of fluorescent conjugated antibodies on the surface of a target cell is affected by the binding affinity of a particular antibody to an antigen. The binding affinity of an antibody is a characteristic that is specific to each antibody-antigen pair. This is especially true of monoclonal antibodies which are selective of the antigens to which they will bind. The affinity is a function of the chemical makeup and structure of the respective binding sites on the antibody and the antigen.

Affinity can be illustrated in terms of binding kinetics. FIG. 10 illustrates the reaction curves for the reaction of two different types of monoclonal antibodies with a single antigen type. Despite the fact that the temperature, antibody concentration, number of antigen binding sites per cell are the same, the two reactions proceed at a different rates. Curve 134 illustrates the rate at which a reaction proceeds when there is a relatively low antibody-antigen affinity ($A_2$). Curve 136 illustrates the rate at which a reaction proceeds when there is a relatively high antibody-antigen affinity ($A_1$). After an incubation time of $t_1$, the reaction with affinity $A_2$ will have two times as many bound antibodies as will the reaction with affinity $A_1$.

FIG. 11 is a graph that plots the peak height for cells labeled with anti-CD4 antibodies conjugated to a fluorescent dye after different incubation times. The Y-axis is the peak intensity. The peak intensity is proportionally related to the number of antigens bound to a cell. Each point along the graph represents the average height of a number of peaks detected at a similar time interval. The longer the sample is allowed to incubate, the closer that the concentration of fluorescent conjugated antibodies will approach a point of saturation.

Lengthening the incubation time prior to scanning may increase the concentration of fluorescent conjugated antibodies on a particular cell, but prolonged incubation has a potentially undesirable side effect, the occurrence of non-specific binding. Non-specific binding is a phenomena where antibodies attach to antigens for which the antibody is not specifically targeted. Antibodies are immunoglobulin molecules that are capable of binding to specific antigens with lock and key compatibility. Normally, certain antibodies will bind to only one type of surface antigen. This particularly true for monoclonal antibodies preferably used for assays in accordance with the present invention. Under certain circumstances, even monoclonal antibodies will bind to surface proteins than the antigen to which it characteristically and specifically binds. Non-specific binding is not a problem in every assay. When it is a factor in a particular assay, the non-specific binding often has less favorable thermodynamic and kinetic properties. Consequently, a shorter incubation period can mitigate non-specific binding.

An increase in the temperature at which incubation occurs can greatly increase the rate at which fluorescent conjugated antibodies bind to target antigens on target cells. The binding of fluorescent conjugated antibodies to antigens in a sample of whole blood at body temperature occurs at a much faster rate than would occur under identical condition at room temperature. Increasing the temperature of a sample is particularly important when the samples are refrigerated prior to analysis.

The binding kinetics is also affected by the concentration of antibodies in the solution. A high concentration of antibodies will permit the cells to reach a saturation point faster. Lower concentrations of antibodies require longer incubation times to reach the same saturation level. When determining the ideal concentration of an antibody, the benefit associated with faster reaction kinetics and higher level of saturation in shorter time is balanced with the resulting higher background noise caused by a higher concentration of unbound antibodies which remain dissolved in the sample.

Factors such as antibody-antigen affinity and antigen population are not necessarily within the skilled artisan's control. Such factors provide limitations on how a sample can be prepared in a scan capillary. Other factors may be adjusted according to the present invention to maximize the ability of a scanner to detect a peak above a cell. The length of incubation, temperature of incubation, and concentration of antibodies in solution are variables that can be manipulated to maximize the fluorescent signal from the target cells marked with antibodies.

EXAMPLE 1

Blood was drawn into an EDTA Vacutainer tube (Becton-Dickenson, San Jose, Calif.) from a healthy human patient. The blood was rocked for five minutes then the cap was removed. One hundred microliters ($\mu$l) was removed with a precision pipet (Pipetman, Ranin Instruments, Woburn, Mass.) The blood was then placed into a 0.6 ml polypropylene microcentrifuge tube. In the bottom of the tube, two dye labeled antibodies had been dried down. The first anti-CD4 (Leu-3a, Becton-Dickenson) was conjugated with "CY5.5" dye (BDS Systems, Inc.) and the second was anti-CD3 (Becton Dickenson) conjugated with "CY5.0" (BDS Systems, Inc.). To preserve their integrity, the antibodies were dried down as part of a 2% bovine serum and 4% sucrose solution. When reconstituted with the 100 $\mu$l of blood, the final antibody concentrations were 1.0 micrograms per milliliter ($\mu$g/ml) and 1.5 $\mu$g/ml.

The microcentrifuge tube was vortexed for five seconds to mix in the antibodies and then allowed to incubate for 20 minutes. A glass microcapillary (Vitro Dynamics Inc., Rockaway, N.J.) with the dimensions of 0.038×0.40×60.0 millimeters (mm) was placed horizontally on a plastic holder. After the 20 minute incubation, the blood was vortexed for five seconds. A ten microliter drop was then pipetted onto one end of the capillary, The solution was wicked into the capillary in approximately one minute. The center 40 millimeters of the capillary was then interrogated by the HeNe based scanning device as described herein.

FIG. 12 is a two dimensional scatter plot generated from the interrogation of the sample. Each point on the scatter plot represents a detected peak by the imaging instrument. The ratio of fluorescent intensity on the Y-axis to the fluorescent intensity on the X-axis distinguishes subpopulations of cells. Due to the uneven hematocrit layer, the cells are virtually indistinguishable.

EXAMPLE 2

The same procedure in Example 1 was followed except that a detergent (Zwittergent 3-08, Calibochem, Inc.) was dried down with the antibodies. When rehydrated with the blood it was present at a concentration of 30 millimolar.

The addition of the zwitterionic detergent creates an even hematocrit layer. FIG. 13 represents a scatter plot of the sample prepared according to the method of Example 2. The scatter plot shows three distinct subpopulations of cells. Population 200 are cells that are CD4+/CD3+. Population 202 are cells that are CD3+ only. Population 204 is background noise. Thus, the addition of the reagent allows adequate enumeration of the target component.

EXAMPLE 3

The same procedure described in Example 1 was followed through the incubation step. At this point 174 microliters of phosphate buffered saline solution containing two percent bovine serum was added to the incubated blood and vortexed. Ten microliters of the diluted blood was then dropped onto the end of a 0.10×0.67×60 millimeter glass microcapillary (Vitro Dynamics, Inc.) and the microcapillary filled by capillary action in about 15 seconds.

FIG. 14 represents a scatter plot of the sample prepared according to the method of Example 3. The addition of the buffered solution creates an even hematocrit layer. The scatter plot shows three distinct subpopulations of cells. Population 206 are cells that are CD4+/CD3+. Population 208 are cells that are CD3+ only. Population 210 is background noise. Again, the target component is enumerated properly by the imaging instrument.

EXAMPLE 4

One hundred milliliters of anticoagulated veinous blood was incubated with CD4 monoclonal antibody (Leu-3a, Becton-Dickenson) conjugated with "CY5.5" dye at a concentration of 1.0 microgram per milliliter ($\mu$g/ml). After the 20 minute incubation, 100 microliters of blood was added to four microcentrifuge tubes. These were then spun at 1000 rpm for ten minutes to separate the plasma from the cells. The first tube was left intact. Ten microliters of plasma was removed from the second tube, 20 microliters from the third tube and 30 microliters from the fourth tube. The samples were then vortexed for five seconds.

The hematocrit concentration was measured for each sample using a Statspin 3 instrument (Statspin Technologies, Norwood, Mass.). Ten microliters of each sample was then placed on a 0.1×0.67×80.0 millimeter capillary and then 40 millimeters in the center of the capillary was scanned using the imaging instrument. Since the capillary is 100 $\mu$m thick, the hematocrit percentage can be converted directly to a micron thickness of hematocrit in the capillary. FIGS. 15–18 respectively show histograms of peak intensity versus number of cells for the four hematocrit levels. The CD4 population is clearly distinguished above the background noise at the 46 and 52 percent hematocrit levels but cannot be distinguished at the 60 or 80 percent levels. Thus, it is necessary to reduce the hematocrit layer to less than about sixty microns.

EXAMPLE 5

Blood samples from twenty-one patients were assayed for CD4 using the method described in Example 1. The samples from the same patients were analyzed for CD4 using a FACS Scan flow cytometer (Becton Dickenson, San Jose, Calif.). Procedures and reagents supplied by the manufacture were used to do the flow cytometer analysis. The slope of the regression line was 1.051. The "R squared" correlation between the two methods was 0.994. FIG. 19 is a plot illustrating the regression analysis.

While several particular forms of invention have been illustrated and described, it will be apparent that various modifications can be made without departing from the spirit and scope of the invention. Accordingly, it is not intended that the invention be limited, except as by the appended claims.

We claim:

1. A method of enumerating target components in a sample containing blood particles, comprising the steps of:
   providing the sample containing blood particles;
   staining the sample with a fluorescent compound configured to selectively bind to the target components of the sample;
   adding a reagent to the blood particles in the sample to evenly distribute the blood particles within the sample without separating any of the blood particles from the sample;
   placing the sample in a sample holder such that the blood particles within the sample holder form an even layer of blood particles that is greater than one particle deep, wherein the sample holder has a depth in the range of ten to two hundred microns;
   exciting the fluorescent compound with light having an excitation wavelength causing the fluorescent compound to fluoresce; and
   detecting and enumerating the target components.

2. The method of claim 1, wherein the target components are a cell subpopulation.

3. The method of claim 1, wherein the target components are white blood cells.

4. The method of claim 1, wherein the target components are viruses.

5. The method of claim 1, wherein the target components are platelets.

6. The method of claim 1, wherein the target components are bacteria.

7. The method of claim 1, wherein the target components are lymphocytes.

8. The method of claim 1, wherein the target components are DNA molecules.

9. The method of claim 1, wherein the staining step includes binding the fluorescent compound to an RNA molecule within the target components.

10. The method of claim 1, wherein the staining step is performed after the adding a reagent step.

11. The method of claim 1, wherein the adding a reagent step includes adding a diluent to the sample.

12. The method of claim 1, wherein the adding a reagent step includes adding an isotonic saline solution to the sample.

13. The method of claim 1, wherein the adding a reagent step includes adding a hypotonic solution to the sample.

14. The method of claim 1, wherein the adding a reagent step includes adding a reagent to the sample which changes the pH of the sample.

15. The method of claim 1, wherein the adding a reagent step includes adding a detergent to the sample.

16. The method of claim 1, wherein the adding a reagent step includes adding an alkyl zwitterionic compound to the sample.

17. The method of claim 1, wherein the adding a reagent step includes adding a compound having the formula n-Octyl-N,N-dimethyl-3-ammonio-1-propanesulfonate to the sample.

18. The method of claim 1, wherein the adding a reagent step includes adding a dried reagent that does not substantially affect an initial volume of the sample.

19. The method of claim 1, wherein the light is laser light having a wavelength greater than five hundred and fifty (550) nanometers.

20. The method of claim 1, wherein the fluorescent compound has an emission wavelength greater than five hundred and fifty (550) nanometers.

21. The method of claim 1, wherein the fluorescent compound has an emission wavelength in the range of 650 to 700 nanometers.

22. A method of analyzing a static blood sample containing blood components on a analysis by a fluorescent imaging instrument, comprising the steps of:
   obtaining a blood sample;
   incubating a fluorescent compound with the blood sample such that the fluorescent compound binds to target components of the blood sample;
   placing a portion of the blood sample into a chamber of predetermined volume, wherein the blood sample provides a substantially uniform layer of blood components that is greater than one particle deep; and
   scanning the sample in a two dimensional region to detect and enumerate the target components.

23. The method of claim 22, wherein the step of placing a portion of the blood sample comprises placing a portion of the blood sample into the chamber wherein the depth of the layer of blood components is in the range of five to sixty microns.

24. The method of claim 22, wherein the step of placing a portion of the blood sample into a chamber comprises placing a portion of the blood sample into a scan capillary having a depth in the range of ten to two hundred microns.

25. The method of claim 22, wherein the step of placing a portion of the blood sample into a chamber comprises placing a portion of the blood sample into a scan capillary having a depth of one hundred microns.

26. The method of claim 22, wherein the fluorescent compound has an emission wavelength greater than five hundred nanometers.

27. The method of claim 22, wherein the fluorescent compound has a peak emission wavelength of 650 to 700 nanometers.

28. The method of claim 22, wherein the fluorescent compound is a cyanine dye bound to a monoclonal antibody.

29. The method of claim 22, further comprising the step of adding a known number of microparticles to the blood sample to determine a volume of blood sample in the chamber.

30. An assay for enumerating target components in a whole blood sample, comprising the steps of:
   providing a whole blood sample containing blood components;
   staining the whole blood sample with a fluorescent compound configured to selectively bind to target components of the whole blood sample;
   adding a reagent to the whole blood sample to prevent red blood cells within the whole blood sample from aggregating without separating any of the blood components from the whole blood sample;
   placing the sample in a container;
   exciting the fluorescent compound with light; and
   detecting and enumerating target components.

31. The method of claim 30, wherein the exciting the fluorescent compound step comprises illuminating the fluorescent compound with laser light having a wavelength greater than 550 nanometers.

32. The method of claim 30, wherein the laser light has a peak wavelength in the range of 600 to 650 nanometers.

33. A static sample preparation insertable into a scanner that scans over a two dimensional area and that detects and enumerates target components, the static sample preparation comprising:

a chamber having a depth in the range of ten to two hundred microns;

particles including target components; and a fluorescent complex that is selected to bind to the target components, wherein the particles and the fluorescent complex are disposed in the chamber and have an even layer of static particles that is greater than one particle deep.

34. The static sample preparation of claim 33, wherein the chamber is a scan capillary.

35. The static sample preparation of claim 33, wherein the chamber is a scan capillary having a depth of one hundred microns.

36. A static sample preparation insertable into a scanner that scans over a two dimensional area and that detects and enumerates target components, the static sample preparation comprising:

a chamber;

particles including target components; and a fluorescent complex that is selected to bind to the target components wherein the particles and the fluorescent complex are disposed in the chamber and have an even layer of static particles that is greater than one particle deep and wherein the fluorescent complex includes a fluorescent dye bound to an antibody specific to an antigen expressed on the target components.

37. The sample preparation of claim 33, further comprising a reagent which inhibits aggregation of red blood cells without separating any of the blood component from the whole blood sample.

38. The sample preparation of claim 37, wherein the reagent is an isotonic saline solution.

39. The sample preparation of claim 37, wherein the reagent is a detergent.

40. The sample preparation of claim 37, wherein the reagent is an alkyl zwitterionic compound.

41. The sample preparation of claim 37, wherein the reagent has the formula n-Octyl-N,N-dimethyl-3-ammonio-1-propanesulfonate.

42. A method of analyzing a sample containing particles including target components with a fluorescent imaging instrument, comprising the steps of:

obtaining a sample;

incubating a fluorescent compound with the sample such that the fluorescent compound binds to a target component of the sample;

placing a portion of the sample into a sample holder, the sample holder having a layer of particles that are greater than one particle deep; and scanning the sample over a two dimensional area to detect and enumerate the target components.

43. The method of claim 42 further comprises the step of calculating the volume of fluid in the two dimensional area.

44. The method of claim 42 wherein the scanning step includes scanning with a laser light having a wavelength greater than 550 nanometers.

45. The method of claim 42 wherein the scanning step includes scanning with a laser light that has a peak wavelength in the range of 600 to 650 nanometers.

46. The method of claim 42 wherein the placing step includes placing a portion of the mixture into a chamber wherein the particles form a layer that is less than 60 microns deep.

47. The method of claim 42 wherein the placing step includes placing a portion of the mixture into a scan capillary having a depth that is less than 200 hundred microns.

48. The method of claim 42 further comprising the step of adding a reagent that causes even distribution of the particles by preventing aggregation of the particles without separating any of the particles from the sample.

* * * * *

UNITED STATES PATENT AND TRADEMARK OFFICE
CERTIFICATE OF CORRECTION

PATENT NO. : 5,932,428                          Page 1 of 2
DATED : August 3, 1999
INVENTOR(S) : Robert S. Dubrow et al.

It is certified that error appears in the above-identified patent and that said Letters Patent is hereby corrected as shown below:

Column 1,
Line 10, "May 19, 1994" should read -- May 2, 1994 --.

Column 5,
Line 54, "PH" should read -- pH --.

Column 6,
Line 1, "baseline layer." should read -- baseline. --.

Column 8,
Line 63, "such as a target in its path." should read -- such as a target cell 80, in its path. --.

Column 13,
Line 2, "weak the adhesive" should read -- weak adhesive --.
Line 3, "is not," should read -- is not --.

Column 14,
Line 64, "urchased under" should read -- purchased under --.

Column 15,
Line 22, "light hen" should read -- light when --.

Column 16,
Line 40, "laser 34" should read -- laser light 34 --.

UNITED STATES PATENT AND TRADEMARK OFFICE
CERTIFICATE OF CORRECTION

PATENT NO. : 5,932,428
DATED : August 3, 1999
INVENTOR(S) : Robert S. Dubrow et al.

It is certified that error appears in the above-identified patent and that said Letters Patent is hereby corrected as shown below:

<u>Column 22, claim 22,</u>
Line 8, "on a analysis by a" should read -- for analysis by a --.

Signed and Sealed this

Ninth Day of April, 2002

Attest:

*Attesting Officer*

JAMES E. ROGAN
*Director of the United States Patent and Trademark Office*